(12) United States Patent
Soukos et al.

(10) Patent No.: US 10,463,879 B2
(45) Date of Patent: Nov. 5, 2019

(54) ANIMAL PHOTOTHERAPEUTIC SYSTEM

(71) Applicants: The Forsyth Institute, Cambridge, MA (US); Nikolaos S. Soukos, Saugus, MA (US); J. Max Goodson, Cambridge, MA (US)

(72) Inventors: Nikolaos S. Soukos, Saugus, MA (US); J. Max Goodson, Cambridge, MA (US)

(*) Notice: Subject to any disclaimer, the term of this patent is extended or adjusted under 35 U.S.C. 154(b) by 0 days.

(21) Appl. No.: 15/593,018

(22) Filed: May 11, 2017

(65) Prior Publication Data

US 2017/0326383 A1    Nov. 16, 2017

Related U.S. Application Data

(60) Provisional application No. 62/334,673, filed on May 11, 2016.

(51) Int. Cl.
*A61N 5/06*    (2006.01)

(52) U.S. Cl.
CPC ......... *A61N 5/0624* (2013.01); *A61N 5/0603* (2013.01); *A61N 2005/0606* (2013.01); *A61N 2005/0626* (2013.01); *A61N 2005/0642* (2013.01); *A61N 2005/0651* (2013.01); *A61N 2005/0659* (2013.01); *A61N 2005/0662* (2013.01); *A61N 2005/0663* (2013.01)

(58) Field of Classification Search
CPC ................ A61N 5/0624; A61N 5/0603; A61N 2005/0606; A61N 2005/0626; A61N 2005/0642; A61N 2005/0651; A61N 2005/0659; A61N 2005/0662; A61N 2005/0663

USPC .......................................................... 607/92
See application file for complete search history.

(56) References Cited

U.S. PATENT DOCUMENTS

| 5,500,635 A | 3/1996 | Mott |
| 5,971,827 A | 10/1999 | Lee et al. |
| 2003/0142489 A1 | 7/2003 | Cooper et al. |

(Continued)

OTHER PUBLICATIONS

International Search Report and Written Opinion for International Application No. PCT/US2017/032212 dated Sep. 12, 2017.

*Primary Examiner* — John R Downey
(74) *Attorney, Agent, or Firm* — Hathaway Russell; Erik A. Huestis; Foley Hoag, LLP

(57) ABSTRACT

Light-based systems and methods are provided with targeted antibacterial action for mouth care in animals such as dogs. In various embodiments, the device includes a substantially impermeable shell. The shell has an outer surface. The outer surface has at least one substantially transparent region. The device further includes at least one light-emitting diode disposed within the shell. The at least one light-emitting diode is adapted to emit light having a wavelength between about 400 nm and about 1,000 nm when powered. The at least one light-emitting diode is configured to provide an average light intensity of between about 10 and about 50 mW/cm$^2$ across the at least one substantially transparent region of the outer surface. The device further includes a power source disposed within the shell. The device further includes a switch at least partially disposed within the shell and adapted to control current flow from the power source to the at least one light-emitting diode.

29 Claims, 13 Drawing Sheets

(56) References Cited

U.S. PATENT DOCUMENTS

| | | | |
|---|---|---|---|
| 2005/0004631 A1* | 1/2005 | Benedict | A61N 5/0619 607/88 |
| 2005/0182460 A1 | 8/2005 | Kent et al. | |
| 2007/0259310 A1* | 11/2007 | Goodson | A61C 1/088 433/29 |
| 2008/0255498 A1 | 10/2008 | Houle | |
| 2009/0036955 A1* | 2/2009 | Han | A61F 9/008 607/89 |
| 2012/0064480 A1* | 3/2012 | Hegemann | A61C 17/0202 433/82 |
| 2012/0148976 A1* | 6/2012 | Brawn | A61C 7/06 433/24 |
| 2012/0275843 A1* | 11/2012 | Jimenez | A46B 11/0006 401/268 |
| 2012/0294620 A1 | 11/2012 | Meyer et al. | |
| 2013/0042876 A1* | 2/2013 | Hermanson | A61F 5/566 128/848 |
| 2013/0117950 A1* | 5/2013 | Kim | A61C 17/221 15/22.1 |
| 2013/0327327 A1* | 12/2013 | Edwards | A61M 15/0028 128/203.11 |
| 2013/0344454 A1* | 12/2013 | Nath | A61N 5/0616 433/29 |
| 2014/0121594 A1* | 5/2014 | Connor | A61F 5/0006 604/77 |
| 2015/0112411 A1 | 4/2015 | Beckman et al. | |
| 2016/0045760 A1 | 2/2016 | Tapper et al. | |

* cited by examiner

ANIMAL PHOTOTHERAPEUTIC SYSTEM

CROSS-REFERENCE TO RELATED APPLICATIONS

This application claims the benefit of U.S. Provisional Application No. 62/334,673, filed May 11, 2016, which is hereby incorporated by reference in its entirety.

BACKGROUND

Embodiments of the present disclosure relate to phototherapeutic systems, and more specifically, to light-based systems with targeted antibacterial action for mouth care in animals such as dogs or cats.

BRIEF SUMMARY

According to various embodiments of the present disclosure, devices for phototherapy are provided. In various embodiments, the device includes a substantially impermeable shell. The shell has an outer surface. The outer surface has at least one substantially transparent region. The device further includes at least one light-emitting diode disposed within the shell. The at least one light-emitting diode is adapted to emit light having a wavelength between about 400 nm and about 1,000 nm when powered. The at least one light-emitting diode is configured to provide an average light intensity of between about 10 and about 50 mW/cm$^2$ across the at least one substantially transparent region of the outer surface. The device further includes a power source disposed within the shell. The device further includes a switch disposed at least partially within the shell and adapted to control current flow from the power source to the at least one light-emitting diode.

In some embodiments, the substantially transparent region is substantially transparent to light having a wavelength of about 400 nm to about 1,000 nm.

In some embodiments, the at least one light-emitting diode is adapted to emit light having a wavelength between about 400 nm and about 700 nm when powered. In some embodiments, the at least one light-emitting diode is adapted to emit light having a wavelength between about 400 nm and about 500 nm when powered. In some embodiments, the at least one light-emitting diode is adapted to emit light having a wavelength of about 455 nm when powered.

In some embodiments, the shell is substantially spherical. In some embodiments, the shell is substantially toroidal. In some embodiments, the shell comprises a handle portion and a diffuser portion, the at least one substantially transparent region being located on the diffusion portion and the power source being disposed within handle portion. In some embodiments, the handle portion is substantially spherical. In some embodiments, the handle portion is substantially cylindrical. In some embodiments, the handle portion and the diffuser portion are mechanically connected by threads. In some embodiments, the handle portion and the diffuser portion are mechanically connected by a ball joint.

In some embodiments, the device further comprises a strap extending from the handle portion.

In some embodiments, the diffuser portion is substantially cylindrical. In some embodiments, the diffuser portion is substantially conical. In some embodiments, the diffuser portion is substantially a truncated cone. In some embodiments, the diffuser portion has a substantially circular cross section. In some embodiments, the diffuser portion has a substantially ovoid cross section. In some embodiments, the diffuser portion has a substantially annular cross section. In some embodiments, the diffuser portion is substantially annular. In some embodiments, wherein the diffuser portion has a substantially parallelepiped shape.

In some embodiments, the power source comprises a battery. In some embodiments, the device further comprises an inductive coupling port electrically coupled to the power source. In some embodiments, the shell comprises a battery access port. In some embodiments, the battery access port comprises a threaded cap.

In some embodiments, the device further comprises a pressure sensor, the pressure sensor being operatively coupled to the switch. In some embodiments, the pressure sensor is adapted to activate the switch upon detection of pressure exceeding a predetermined value. In some embodiments, the pressure sensor comprises a pressure switch.

In some embodiments, the device further comprises a strain sensor, the strain sensor being operatively coupled to the switch. In some embodiments, the strain sensor comprises a strain gauge, a piezo polymer strain sensor, a NITINOL wire, or a variable resistive wire. In some embodiments, the strain sensor comprises a piezo sensor or a piezoceramic sensor. In some embodiments, the strain sensor is adapted to activate the switch upon detection of strain exceeding a predetermined value. In some embodiments, the strain sensor is embedded in the shell. In some embodiments, the strain sensor is disposed on the shell.

In some embodiments, the device further comprises a strap, the shell being embedded in the strap.

In some embodiments, the device further comprises an IR receiver, the IR receiver being operatively coupled to the switch. In some embodiments, the IR receiver is adapted to activate the switch upon detection of an IR control signal. In some embodiments, the IR receiver is adapted to deactivate the switch upon detection of an IR control signal.

In some embodiments, the device further comprises an RF receiver, the RF receiver being operatively coupled to the switch. In some embodiments, the IR receiver is adapted to activate the switch upon receipt of a control signal. In some embodiments, the IR receiver is adapted to deactivate the switch upon receipt of a control signal. In some embodiments, the RF receiver comprises a Bluetooth receiver.

In some embodiments, the at least one light-emitting diode is disposed within the diffuser portion.

In some embodiments, the at least one light-emitting diode is disposed within the handle portion.

In some embodiments, the device further comprises a reservoir containing a flavoring agent or a medication. In some embodiments, the reservoir is in fluid communication with a pump adapted to dispose the contents of the reservoir on the outer surface.

In some embodiments, the at least one light-emitting diode is configured to provide an average light intensity of about 25 mW/cm$^2$ across the at least one substantially transparent region of the outer surface.

According to various embodiments of the present disclosure, methods for phototherapy are provided. In various embodiments, a device is provided to a non-human animal. The device comprises a substantially impermeable shell, at least one light-emitting diode disposed within the shell, and a power source disposed within the shell. The shell has an outer surface. The outer surface has at least one substantially transparent region. The at least one light-emitting diode is powered from the power source. The at least one light-emitting diode thereby emits light having a wavelength between about 400 nm and about 1,000 nm with an average light intensity of between about 10 and about 50 mW/cm2 across the at least one substantially transparent region of the outer surface of the device.

In some embodiments, the substantially transparent region is substantially transparent to light having a wavelength of about 400 nm to about 1,000 nm.

In some embodiments, the at least one light-emitting diode emits light having a wavelength between about 400 nm and about 700 nm when powered. In some embodiments, the at least one light-emitting diode emits light having a wavelength between about 400 nm and about 500 nm when powered. In some embodiments, the at least one light-emitting diode emits light having a wavelength of about 455 nm when powered.

In some embodiments, the shell is substantially spherical. In some embodiments, the shell is substantially toroidal. In some embodiments, the shell comprises a handle portion and a diffuser portion, the at least one substantially transparent region being located on the diffusion portion and the power source being disposed within handle portion. In some embodiments, the handle portion is substantially spherical. In some embodiments, the handle portion is substantially cylindrical. In some embodiments, the handle portion and the diffuser portion are mechanically connected by threads. In some embodiments, the handle portion and the diffuser portion are mechanically connected by a ball joint.

In some embodiments, the device further comprises a strap extending from the handle portion.

In some embodiments, the diffuser portion is substantially cylindrical. In some embodiments, the diffuser portion is substantially conical. In some embodiments, the diffuser portion is substantially a truncated cone. In some embodiments, the diffuser portion has a substantially circular cross section. In some embodiments, the diffuser portion has a substantially ovoid cross section. In some embodiments, the diffuser portion has a substantially annular cross section. In some embodiments, the diffuser portion is substantially annular. In some embodiments, the diffuser portion has a substantially parallelepiped shape.

In some embodiments, the power source comprises a battery. In some embodiments, the device further comprises an inductive coupling port electrically coupled to the power source. In some embodiments, the shell comprises a battery access port. In some embodiments, the battery access port comprises a threaded cap.

In some embodiments, the device further comprises a pressure sensor, the pressure sensor being operatively coupled to the switch. In some embodiments, the method further comprises activating the switch upon detection of pressure exceeding a predetermined value. In some embodiments, the pressure sensor comprises a pressure switch.

In some embodiments, the device further comprises a strain sensor, the strain sensor being operatively coupled to the switch. In some embodiments, the strain sensor comprises a strain gauge, a piezo polymer strain sensor, a NITINOL wire, or a variable resistive wire. In some embodiments, the strain sensor comprises a piezo sensor or a piezoceramic sensor. In some embodiments, the method further comprises activating the switch upon detection of strain exceeding a predetermined value. In some embodiments, the strain sensor is embedded in the shell. In some embodiments, the strain sensor is disposed on the shell.

In some embodiments, the device further comprises a strap, the shell being embedded in the strap.

In some embodiments, the device further comprises an IR receiver, the IR receiver being operatively coupled to the switch. In some embodiments, the method further comprises activating the switch upon detection of an IR control signal by the IR receiver. In some embodiments, the method further comprises deactivating the switch upon detection of an IR control signal by the IR receiver.

In some embodiments, the device further comprises an RF receiver, the RF receiver being operatively coupled to the switch. In some embodiments, the method further comprises activating the switch upon receipt of a control signal by the RF receiver. In some embodiments, the method further comprises deactivating the switch upon receipt of a control signal by the RF receiver. In some embodiments, the RF receiver comprises a Bluetooth receiver.

In some embodiments, the at least one light-emitting diode is disposed within the diffuser portion. In some embodiments, the at least one light-emitting diode is disposed within the handle portion.

In some embodiments, the method further comprises applying a photodynamic sensitizer to an oral cavity of the non-human animal. In some embodiments, applying the photodynamic sensitizer comprises providing an oral rinse.

In some embodiments, the device further comprises a reservoir containing a flavoring agent or a medication. In some embodiments, the reservoir is in fluid communication with a pump adapted to dispose the contents of the reservoir on the outer surface.

In some embodiments, the light has an average light intensity of about 25 $mW/cm^2$ across the at least one substantially transparent region of the outer surface of the device.

According to various embodiments of the present disclosure, methods for phototherapy are provided. In various embodiments, a wireless control signal is sent from a mobile computing device to an intraoral device. The intraoral device comprises a substantially impermeable shell, at least one light-emitting diode disposed within the shell, and a power source disposed within the shell. The shell has an outer surface. The outer surface having at least one substantially transparent region. In response to the control signal, the at least one light-emitting diode is powered from the power source. The at least one light-emitting diode thereby emits light having a wavelength between about 400 nm and about 1,000 nm with an average light intensity of between about 10 and about 50 mW/cm2 across the at least one substantially transparent region of the outer surface of the device.

In some embodiments, the substantially transparent region is substantially transparent to light has a wavelength of about 400 nm to about 1,000 nm.

In some embodiments, the at least one light-emitting diode emits light having a wavelength between about 400 nm and about 700 nm when powered. In some embodiments, the at least one light-emitting diode emits light having a wavelength between about 400 nm and about 500 nm when powered. In some embodiments, the at least one light-emitting diode emits light having a wavelength of about 455 nm when powered.

In some embodiments, the shell is substantially spherical. In some embodiments, the shell is substantially toroidal. In some embodiments, the shell comprises a handle portion and a diffuser portion, the at least one substantially transparent region being located on the diffusion portion and the power source being disposed within handle portion. In some embodiments, the handle portion is substantially spherical. In some embodiments, the handle portion is substantially cylindrical. In some embodiments, the handle portion and the diffuser portion are mechanically connected by threads. In some embodiments, the handle portion and the diffuser portion are mechanically connected by a ball joint.

In some embodiments, the device further comprises a strap extending from the handle portion.

In some embodiments, the diffuser portion is substantially cylindrical. In some embodiments, the diffuser portion is substantially conical. In some embodiments, the diffuser portion is substantially a truncated cone. In some embodiments, the diffuser portion has a substantially circular cross section. In some embodiments, the diffuser portion has a substantially ovoid cross section. In some embodiments, the diffuser portion has a substantially annular cross section. In some embodiments, the diffuser portion is substantially annular. In some embodiments, the diffuser portion has a substantially parallelepiped shape.

In some embodiments, the power source comprises a battery. In some embodiments, the device further comprises an inductive coupling port electrically coupled to the power source. In some embodiments, the shell comprises a battery access port. In some embodiments, the battery access port comprises a threaded cap.

In some embodiments, the device further comprises a pressure sensor, the pressure sensor being operatively coupled to the switch. In some embodiments, the method further comprises activating the switch upon detection of pressure exceeding a predetermined value. In some embodiments, the pressure sensor comprises a pressure switch.

In some embodiments, the device further comprises a strain sensor, the strain sensor being operatively coupled to the switch. In some embodiments, the strain sensor comprises a strain gauge, a piezo polymer strain sensor, a NITINOL wire, or a variable resistive wire. In some embodiments, the strain sensor comprises a piezo sensor or a piezoceramic sensor. In some embodiments, the method further comprises activating the switch upon detection of strain exceeding a predetermined value. In some embodiments, the strain sensor is embedded in the shell. In some embodiments, the strain sensor is disposed on the shell.

In some embodiments, the device further comprises a strap, the shell being embedded in the strap.

In some embodiments, the device further comprises an IR receiver, the IR receiver being operatively coupled to the switch. In some embodiments, the control signal is received via the IR receiver.

In some embodiments, the device further comprises an RF receiver, the RF receiver being operatively coupled to the switch. In some embodiments, the control signal is received via the RF receiver. In some embodiments, the RF receiver comprises a Bluetooth receiver.

In some embodiments, the at least one light-emitting diode is disposed within the diffuser portion. In some embodiments, the at least one light-emitting diode is disposed within the handle portion.

In some embodiments, the method further comprises applying a photodynamic sensitizer to an oral cavity of the non-human animal. In some embodiments, applying the photodynamic sensitizer comprises providing an oral rinse.

In some embodiments, the device further comprises a reservoir containing a flavoring agent or a medication. In some embodiments, the reservoir is in fluid communication with a pump adapted to dispose the contents of the reservoir on the outer surface.

In some embodiments, the light having an average light intensity of about 25 mW/cm$^2$ across the at least one substantially transparent region of the outer surface of the device.

According to various embodiments of the present disclosure, systems for phototherapy are provided. In various embodiments, a system comprises an intraoral device and a mobile computing device. The intraoral device includes a substantially impermeable shell, at least one light-emitting diode disposed within the shell, and a power source disposed within the shell. The shell has an outer surface. The outer surface has at least one substantially transparent region. The mobile computing device includes a computer readable storage medium having program instructions embodied therewith, the program instructions executable by a processor of the mobile computing device to cause the processor to perform a method. The method includes sending a wireless control signal from a mobile computing device to the intraoral device.

In some embodiments, the substantially transparent region is substantially transparent to light having a wavelength of about 400 nm to about 1,000 nm.

In some embodiments, the at least one light-emitting diode is adapted to emit light having a wavelength between about 400 nm and about 1,000 nm when powered. In some embodiments, the at least one light-emitting diode is adapted to emit light having a wavelength between about 400 nm and about 700 nm when powered. In some embodiments, the at least one light-emitting diode is adapted to emit light having a wavelength between about 400 nm and about 500 nm when powered. In some embodiments, the at least one light-emitting diode is adapted to emit light having a wavelength of about 455 nm when powered.

In some embodiments, the shell is substantially spherical. In some embodiments, the shell is substantially toroidal. In some embodiments, the shell comprises a handle portion and a diffuser portion, the at least one substantially transparent region being located on the diffusion portion and the power source being disposed within handle portion. In some embodiments, the handle portion is substantially spherical. In some embodiments, the handle portion is substantially cylindrical. In some embodiments, the handle portion and the diffuser portion are mechanically connected by threads. In some embodiments, the handle portion and the diffuser portion are mechanically connected by a ball joint.

In some embodiments, the intraoral device further comprises a strap extending from the handle portion.

In some embodiments, the diffuser portion is substantially cylindrical. In some embodiments, the diffuser portion is substantially conical. In some embodiments, the diffuser portion is substantially a truncated cone. In some embodiments, the diffuser portion has a substantially circular cross section. In some embodiments, the diffuser portion has a substantially ovoid cross section. In some embodiments, the diffuser portion has a substantially annular cross section. In some embodiments, the diffuser portion is substantially annular. In some embodiments, the diffuser portion has a substantially parallelepiped shape.

In some embodiments, the power source comprises a battery. In some embodiments, the intraoral device further comprising an inductive coupling port electrically coupled to the power source. In some embodiments, the shell comprises a battery access port. In some embodiments, the battery access port comprises a threaded cap.

In some embodiments, the intraoral device further comprises a pressure sensor, the pressure sensor being operatively coupled to the switch. In some embodiments, the pressure sensor is adapted to activate the switch upon detection of pressure exceeding a predetermined value. In some embodiments, the pressure sensor comprises a pressure switch.

In some embodiments, the intraoral device further comprising a strain sensor, the strain sensor being operatively coupled to the switch. In some embodiments, the strain sensor comprises a strain gauge, a piezo polymer strain sensor, a NITINOL wire, or a variable resistive wire. In some embodiments, the strain sensor comprises a piezo sensor or a piezoceramic sensor. In some embodiments, the strain sensor is adapted to activate the switch upon detection of strain exceeding a predetermined value. In some embodiments, the strain sensor is embedded in the shell. In some embodiments, the strain sensor is disposed on the shell.

In some embodiments, the intraoral device further comprising a strap, the shell being embedded in the strap.

In some embodiments, the intraoral device further comprises an IR receiver, the IR receiver being operatively coupled to the switch. In some embodiments, the wireless control signal is received via the IR receiver.

In some embodiments, the intraoral device further comprises an RF receiver, the RF receiver being operatively coupled to the switch. In some embodiments, the wireless control signal is received via the RF receiver. In some embodiments, the RF receiver comprises a Bluetooth receiver.

In some embodiments, the at least one light-emitting diode is disposed within the diffuser portion. In some embodiments, the at least one light-emitting diode is disposed within the handle portion.

In some embodiments, the device further comprises a reservoir containing a flavoring agent or a medication. In some embodiments, the reservoir is in fluid communication with a pump adapted to dispose the contents of the reservoir on the outer surface.

In some embodiments, the at least one light-emitting diode being configured to provide an average light intensity of between about 10 and about 50 mW/cm$^2$ across the at least one substantially transparent region of the outer surface. In some embodiments, the at least one light-emitting diode being configured to provide an average light intensity of about 25 mW/cm$^2$ across the at least one substantially transparent region of the outer surface.

DETAILED DESCRIPTION

Figure 1:
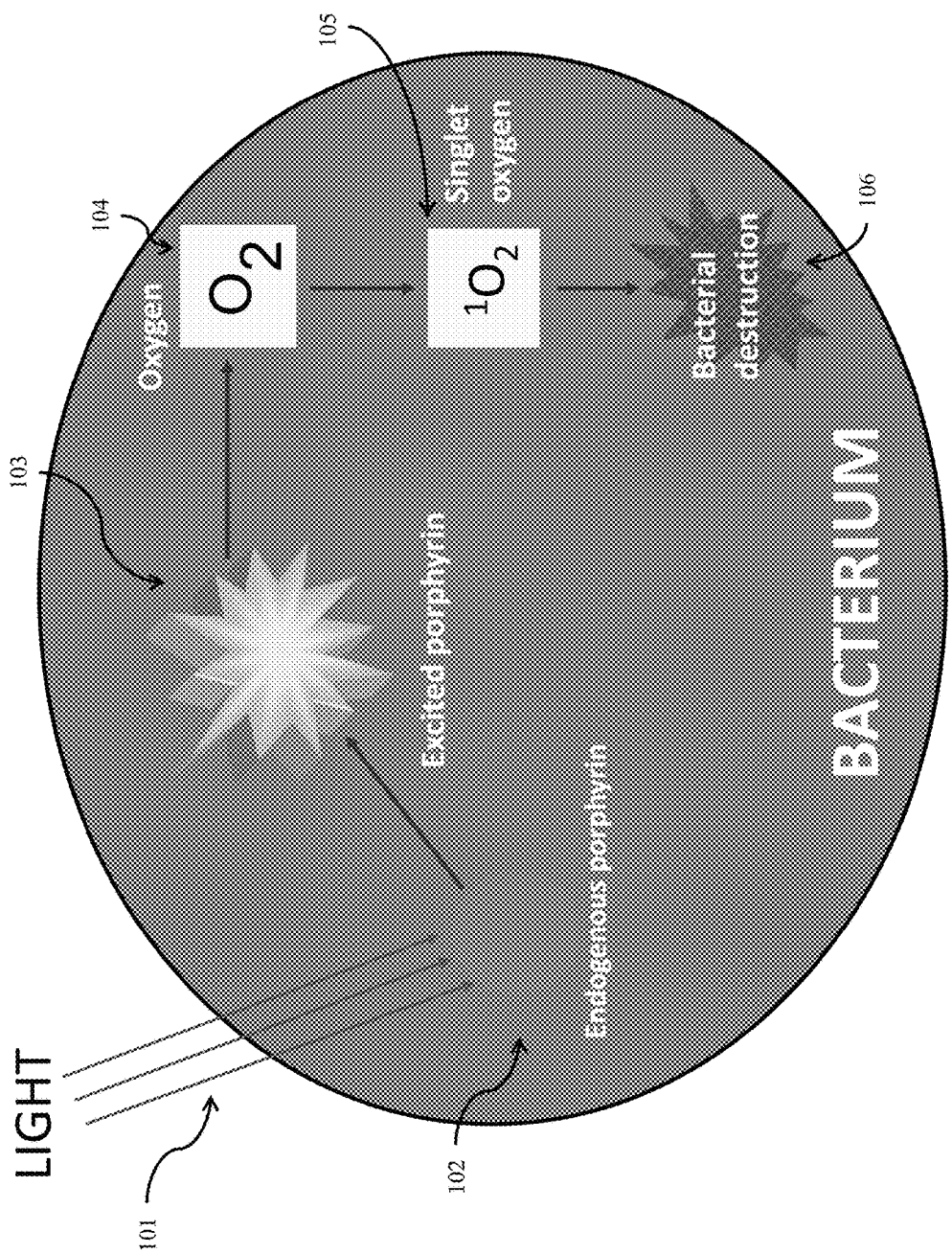
FIG. 1 illustrates the activation of porphyrins within certain bacterial species and the creation of reactive singlet oxygen species leading to bacterial death.

The present disclosure relates to the use of light-based systems with targeted antibacterial action for mouth care in animals. In various embodiments, devices, systems, and methods are provided for treatment of bad breath (halitosis) and gum disease in dogs.

Virtually all animals with teeth are affected by periodontal disease. One generally familiar example is the occurrence oral disease in pets, especially dogs. By three years of age, most dogs have some evidence of periodontal disease accompanied by bad breath. Periodontal diseases include gingivitis (inflammation/redness of the gum) and periodontitis (loss of soft tissue and bone around the tooth). Dental plaque, a sticky coating (film) that builds up on dogs' teeth and contains billions of bacteria, is the causative agent of periodontal diseases. Minerals in the saliva harden the plaque into dental calculus (tartar), which is firmly attached to the teeth. Plaque bacteria under the gum line irritate and cause damage to the supporting tissues around the tooth thus leading to tooth loss. The same bacteria stimulate gum's immune system. Some microorganisms from dental plaque can also enter the bloodstream and are carried around the body. In humans, gum disease (periodontitis) has been suggested as a risk factor for stroke, pneumonia and heart disease. In humans, it may worsen diabetes or may bring early labor.

The microbiology of human gum disease is characterized by the presence of *Prevotella* and *Porphyromonas* species which are thought to be key periodontal pathogens. These species also contain blue light absorbing porphyrins. The effects of these bacteria in humans include gingival inflammation, underlying bone loss and halitosis.

Porphyrin-containing bacteria usually represent less than 10% of the total oral microbiota. Despite their low abundance, the single species *Porphyromonas gingivalis* can disrupt host-microbial homeostasis. Hence, these bacteria are keystone species that that have community-wide effects on oral microbiota. The oral microbiology of common household pets also contains porphyrin-containing *Prevotella* and *Porphyromonas* species. Pets may act as either human infection vectors or the recipient of human infection in animals. Animal periodontal disease appears similar to that of humans and has served to be as a model in human periodontal research.

Halitosis is generally associated with bacterial growth on the tongue. It is the result of bacterial production of volatile sulfur compounds such as hydrogen sulfide and methyl mercaptin. Bacteria responsible include *Prevotella, Porphyromonas* and *Fusobacterium*, all of which are susceptible to blue light.

There are several home oral hygiene strategies that can be used to help maintain a dog's dental health by minimizing plaque accumulation and preventing the mineralization of plaque to form calculus. Soft and angled toothbrushes are available to assist in brushing back teeth. Finger brushes and toothpastes with various flavors have been employed for maintaining oral health between professional dental examinations. Single-use dental wipes may be rubbed daily on the outside of the teeth for plaque removal. Although they taste terrible, rinses or gels of chlorexidine anti-plaque antiseptics can also be used. Rawhide chews and biscuits that contain anti-tartar ingredient are helpful when they are chewed daily, whereas chew toys may be of benefit when used frequently. All of the above mentioned therapies reduce bacteria by application of antibacterial chemicals or mechanical plaque removal.

It will be appreciated that in view of the drawbacks of purely mechanical or chemical approaches, there remains a need for light-based devices and systems for phototherapy in animals. Accordingly, the present disclosure provides for control of gum disease in animals by intraoral application of light. Microorganisms in the mouth of pets are killed by blue light of the appropriate wavelength due to activation of their endogenous porphyrins and subsequent generation of reactive oxygen species. However, unlike humans, animals cannot be relied upon to dose themselves with light in a controlled, continuous fashion, or achieve a prescribed dose of light over time. Accordingly, various embodiments of the present disclosure provide for opportunistic light dosing.

With reference now to FIG. 1, the activation of porphyrins within certain bacterial species and the creation of reactive singlet oxygen species leading to bacterial death is illustrated. As noted above, in dogs and other animals, subgingival plaque (plaque attached to the tooth below the gum line) includes anaerobic, black-pigmented, Gram-negative bacteria 101 like *Porphyromonas gingivalis, Porphyromonas gulae*, and multiple *Fusobacteria* species. The black pigmentation of these microorganisms results from the presence of endogenous organic compounds known as porphyrins. Porphyrins are involved in a variety of metabolic processes in both prokaryotic and eukaryotic cells, including respiration, photosynthesis, and heme biosynthesis. These porphyrin molecules are photosensitive. Excitation by certain wavelengths of light 102 causes energy transfer 103 from electrons within the porphyrin molecule to molecular oxygen 104 present within cells, which then go on to form reactive oxygen species (ROS) 105 that have the ability to damage lipids, proteins, and nucleic acids, resulting in destruction 106 of the bacteria by reaction between singlet oxygen and sensitive molecular species such as DNA or protein of the bacterium.

The aforementioned black-pigmented bacteria can be killed by blue light of the appropriate wavelength due to the activation of their endogenous porphyrins and subsequent generation of ROS. Daily, short-term exposures of oral tissue to blue light in subjects with gingivitis or periodontitis may reduce the load of key pathogens in plaque, thus resulting in a decrease in microbiota associated with disease. Such photodynamic therapy (PDT) may be used in various applications to kill microorganisms. PDT may be used by itself or in concert with dental cleaning procedures, like brushing and scaling.

In general, porphyrins absorb light in a range between about 400 nm and about 700 nm. In some settings, porphyrins have the greatest absorption at about 405 nm to about 420 nm. Accordingly, various embodiments described herein emit light having wavelengths from about 400 nm and about 1,000 nm. Various embodiments emit light having wavelengths between about 400 nm and about 700 nm. Various embodiments emit light having wavelengths between about 400 nm and about 500 nm. Various embodiments emit light having a wavelength of about 455 nm. In some embodiments, the intensity of light is between about 10 and 50 mW/cm$^2$. In some embodiments, the intensity of light is between about 1 and about 100 mW/cm$^2$. In general, wavelengths that avoid the DNA damage associated with UV light are preferable. Light at about 810 nm (infrared) is beneficial for wound healing. In general, intensities that are low enough to avoid heat development and consequent tissue damage are preferable.

Figure 2:
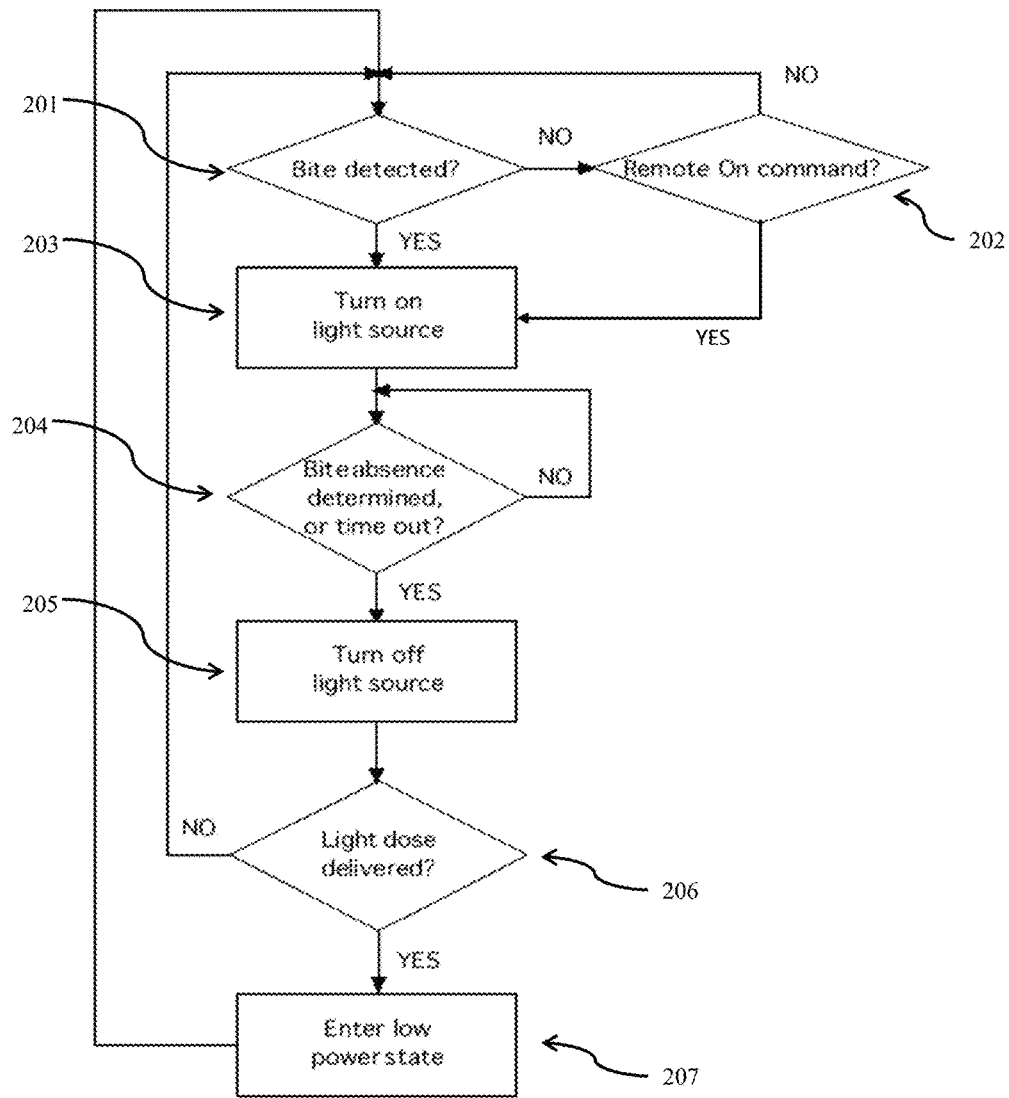
FIG. 2 illustrates a method for treating periodontitis in animals by intraoral application of light according to embodiments of the present disclosure.

Referring now to FIG. 2, a method of oral therapy by intraoral light exposure is illustrated according to embodiments of the present disclosure. Intraoral delivery of light of the appropriate wavelength is provided to trigger superoxide production within the bacterial cell by interacting with those bacteria containing porphyrins and those bacteria that depend on the survival of bacteria containing porphyrins.

When a bite is detected 201 or a remote activation command is received 202, a light source is activated 203. Once the triggering bite ceases or a predetermined time elapses 204, the light source is deactivated 205. In some embodiments, the dosage duration is recorded for later retrieval and analysis. Once a sufficient dosage has been delivered 206, the device may enter a low power state 207 to reduce power consumption. It will be appreciated that this method is suitable for providing treatment using various devices described herein.

By this approach, the natural occurrences of biting force associated with a toy-like delivery systems trigger a timed light exposure which is within the mouth of the animal and has the effect of specifically reducing the number of porphyrin-containing bacteria as well as of those microorganisms depending on the presence of porphyrin-containing bacteria. In some embodiments, treatment light has a wavelength of about 400 nm to about 1000 nm. In some embodiments, the light has a power intensity of about 10 mW/cm$^2$ to about 50 mW/cm$^2$.

Figure 3:
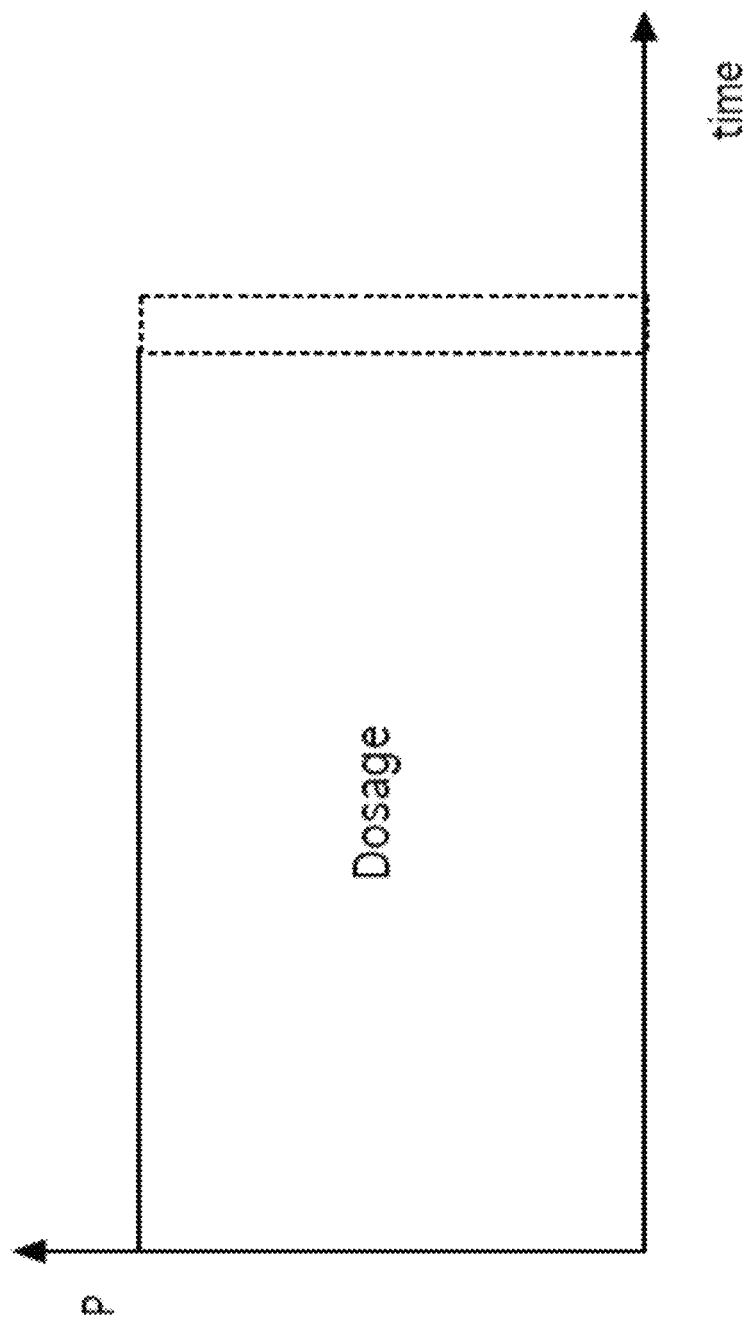
FIG. 3 illustrates an exemplary dosage scheme according to embodiments of the present disclosure.
Figure 4:
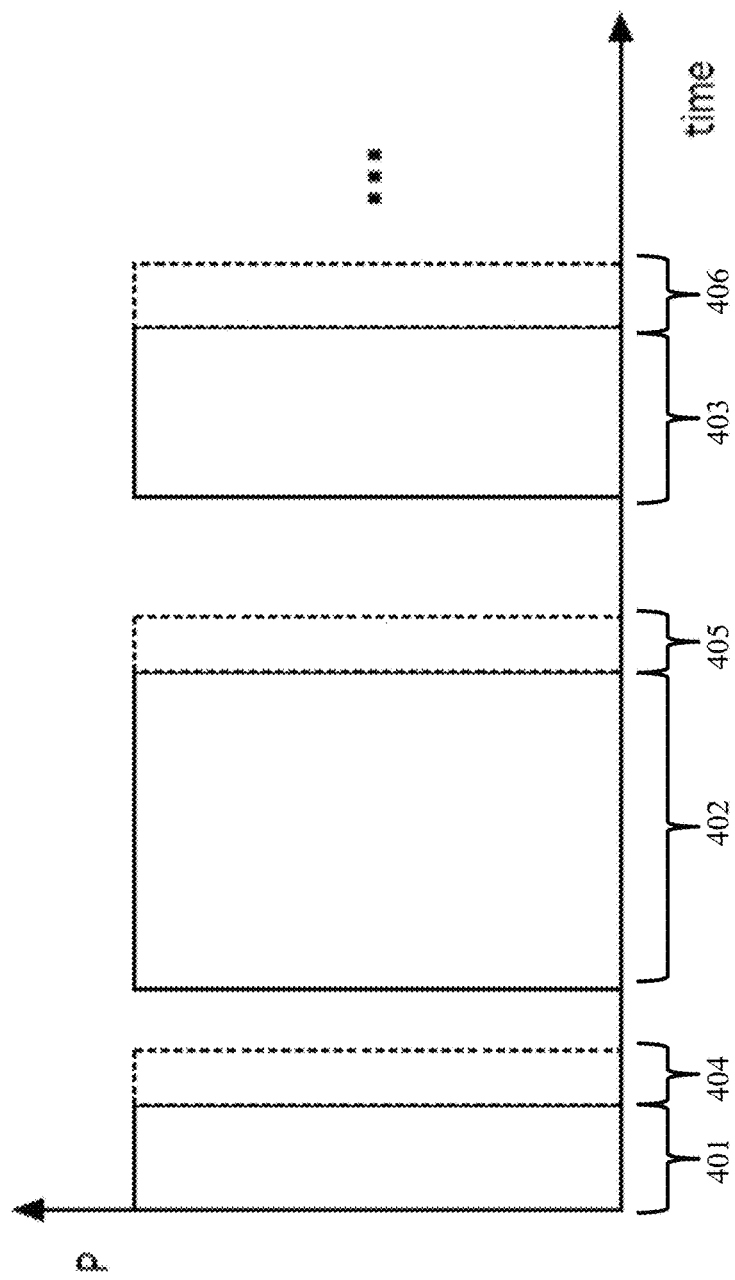
FIG. 4 illustrates another exemplary dosage scheme according to embodiments of the present disclosure.

Referring now to FIGS. 3-4, exemplary dosage schemes are illustrated according to the present disclosure. Various embodiments provide for delivery of a dose of optical energy to the intraoral cavity of a subject such as a dog. This dose may be defined as the product of the optical power P and the time over which the dose is delivered. For a fixed power, time therefore defines the total dosage. As shown in Figure FIG. 3, this corresponds to the area under the curve of delivered optical power P versus time.

In various embodiments, it is advantageous to deliver about 10-50 mW/cm$^2$. In some embodiments, the intensity is between about 1 and about 100 mW/cm$^2$. At an exemplary intensity of 25 mW/cm$^2$, in two minutes, the energy fluence will be 3 J/cm$^2$. Accordingly, various may provide power density of between 1 and about 100 mW/cm$^2$, with an exposure time of between about 5 seconds and about 1 hour, resulting in an energy fluence of about 0.1 to about 1,000 J/cm$^2$. In various embodiments, treatment may be provided about 2-3 times a day.

Unlike humans, animals cannot be relied upon to dose themselves in a controlled, continuous fashion. Accordingly, light dosing according to various embodiments of the present disclosure is opportunistic, and depends on how the animal interacts with devices herein described. Referring to FIG. 4, an animal may bite or chew a light diffuser, guide, or waveguide in any of the disclosed embodiments intermittently over time periods 401, 402, 403. In various embodiments, a sensor sensing the bite causes LED lights to turn on and off. In some embodiments, the LED lights may remain powered on for a period of time 404, 405, 406 after the sensor indicates that the animal is no longer biting or chewing the light diffuser. In this way, light delivery into the oral cavity is continued in case the diffuser is still in the animal's mouth. In some embodiments, the LED lights are activated for a fixed duration after a bite or chew of the light diffuser is sensed.

In some embodiments, a dose is delivered only until the sum of all recent doses meets or exceeds the prescribed total dose. In some embodiments, a dose is delivered at least until the sum of all recent doses meets or exceeds the prescribed total dose. The prescribed dose may be specified as a cumulative dose time assuming a fixed optical power output. When this prescribed dose is achieved, the embodiments may flash their LEDs, inform the human user remotely via an RF signal transmitted to a smart phone, buzz a buzzer, flash a completion-indicating LED, or otherwise notify a human user of completion. Dosage records may be maintained on the device, or transmitted to a smart phone or other mobile device. The mobile device may then in turn maintain a record of doses, dates, and times. Dosage records may also be transmitted to remote computing nodes for storage in a data store such as a database.

Embodiments described herein include light-based devices for prophylactic treatment of periodontal disease in dogs through intraoral application of light. By employing light in the activation of organic compounds within the disease-causing bacteria themselves, treatment is provided to the animal simply by encouraging the use of a device/toy that many animals already routinely use. It will be appreciated that various exterior form factors are suitable according to the present disclosure.

Various embodiments of the present disclosure have portable forms as set forth below. In general, each is adapted to deliver a dose of light having a wavelength of about 400 nm to about 1,000 nm into the intraoral cavity. In some embodiments, wavelengths of about 455 nm are provided. In general, various embodiments are adapted to provide opportunistic light dosing, as animals cannot be relied upon to dose themselves in a controlled, continuous fashion, or to achieve a prescribed dose of light over time.

Figure 5:
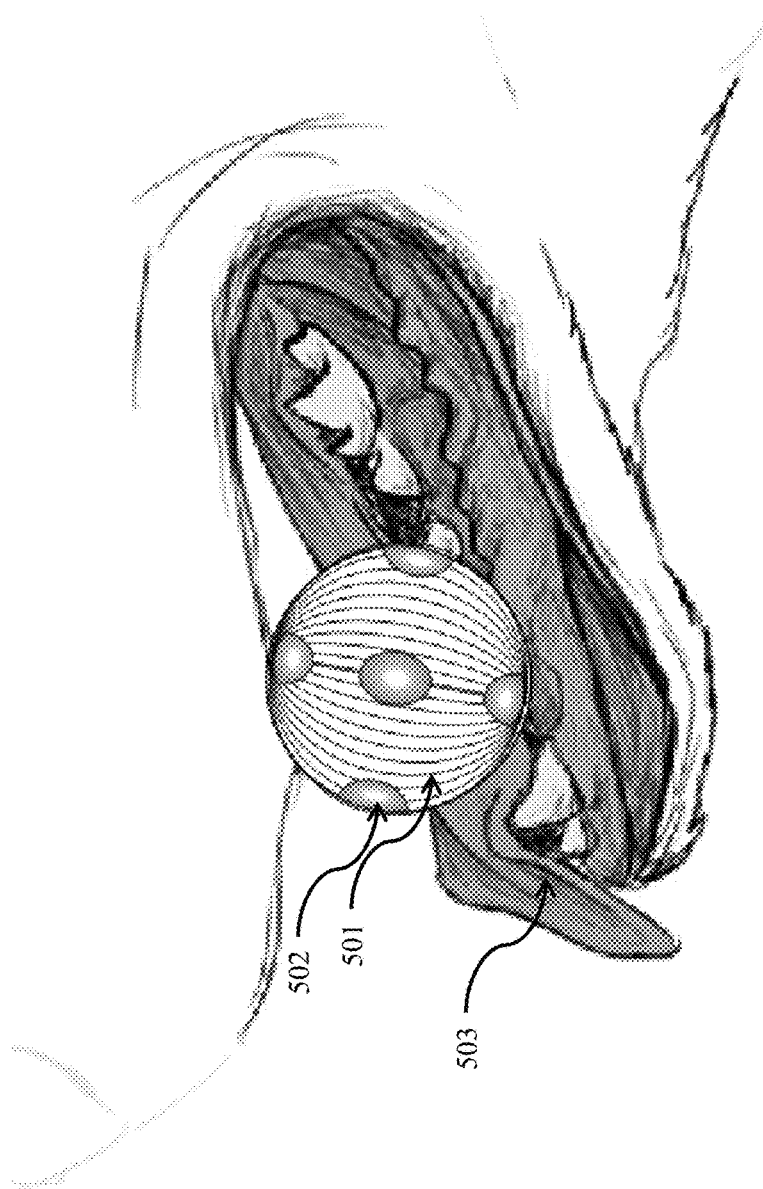
FIG. 5 depicts a device for intraoral application of light according to embodiments of the present disclosure.

With reference now to FIG. 5, a first exemplary device according to the present disclosure is illustrated. A ball 501 emits light of the appropriate wavelength when used as an animal toy. In some embodiments, intraoral light exposure is provided by LEDs 502 embedded in a translucent or transparent plastic ball. In some embodiments, a spherical radiation pattern may be approximated with six light emitting diodes (LEDs) 502; four around the girdle and two on the poles.

In some embodiments, the irradiation may be initiated by either a biting force on the ball, remote triggering via a command received in a radio frequency (RF) or infrared (IR) signal, or by a manual switch mounted on or in the ball. In some embodiments, an increase in compressive or shearing force above a threshold, or operation of a manual switch, will turn on the light source for a fixed period of time. To irradiate the gingival tissues during play, the animal bites the ball and the light turns on to irradiate tissues where harmful bacteria live in the mouth.

In some embodiments, the ball contains a battery, pressure sensor or pressure switch, and one or more light emitting diodes. The ball radiates blue light when the ball is chewed. The battery may be replaceable or rechargeable and may include an audible alarm if the surface is penetrated to prevent harm from chewing the electronics.

Figure 6:
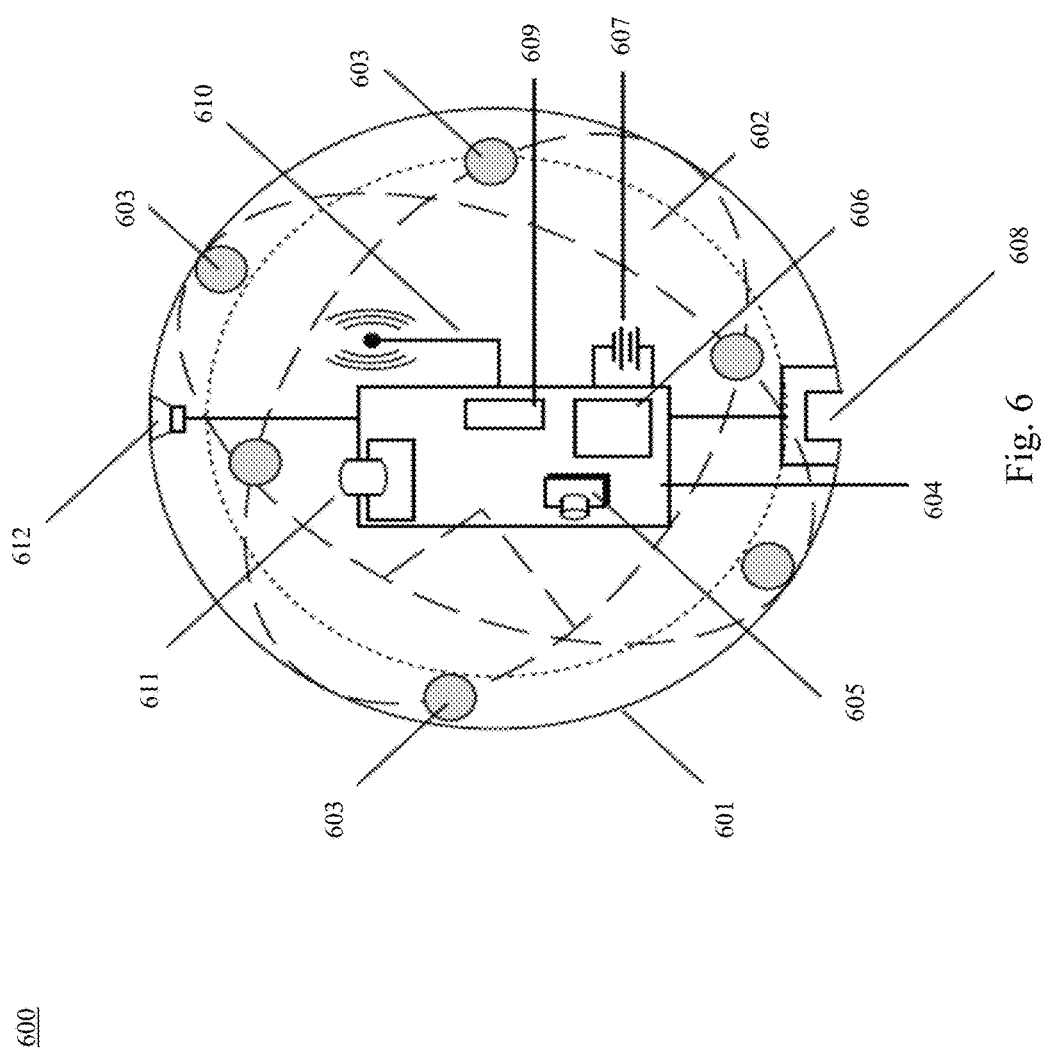
FIG. 6 is an interior schematic view of a device for intraoral application of light according to embodiments of the present disclosure.

Referring to FIG. 6, an interior schematic view of a substantially spherical embodiment is provided. A generally spherical optical diffuser 601 having an inner cavity 602 is illuminated at one end by one or more light sources 603 arrayed around the diffuser. The optical diffuser forms a shell around the other components, and at least a portion of its outer surface is transparent. In various embodiments, light sources 603 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. LEDs 603 may be placed on the diffuser, embedded within the diffuser, or arrayed within the diffuser's cavity 602. The optical diffuser may be flexible, and generally distributes light radially. In some embodiments, the light diffuser may be oblate or prolate spheroidal in shape in order to encourage interaction by the animal and assist in the distribution of light into the intraoral cavity. In some embodiments, diffuser 601 may be substantially or completely transparent.

In some embodiments, the LEDs radiate light at a wavelength of about 400 nm to about 1,000 nm. In some embodiments, one or more LEDs primarily radiate light at about 455 nm, e.g., blue light, while other LEDs radiate light at about 815 nm, e.g., near infrared light.

A pressure sensor 605, such as a solid state pressure sensor, is contained within the cavity. In some embodiments, the pressure sensor may be a pressure switch. The pressure sensor senses when the flexible optical diffuser is squeezed by the closing of an animal's jaws around at least some portion of the diffuser. The pressure sensor may be mounted on a circuit board 604, and its output provided to a circuit 606 that turns on the LEDs when the output of the pressure sensor exceeds a preset value indicative of a biting action that compresses or flexes the optical diffuser.

One of skill in the art will appreciate that circuit 606 may have various designs, and may comprise, e.g., a voltage comparator. Alternatively, circuit 606 comprises a microcontroller programmed to turn on the LEDs when the output of the pressure sensor exceeds a predetermined value indicative of a biting action that compresses or flexes the optical diffuser, or when the microcontroller senses that the output of the pressure switch goes high or low. If the circuit 606 comprises a microcontroller said microcontroller may monitor the charging level of the power source 607. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 606 includes an analog timing circuit comprising a 555 one-shot timer, a CMOS 4060 binary counter, or other analog components and circuits adapted to provide timed activation of the LEDs. In some embodiments, circuit 606 includes a microcontroller having one or more internal counter or timers, software timing loops, or interfaces to outboard counter or timer circuits.

The electronics are contained substantially within the cavity 602. The electronics are powered by batteries 607, which in some embodiment are Lithium ion AA batteries. The batteries may be manually replaceable, or may be charged inductively through an inductive coupling port 608 and associated circuitry.

In some embodiments, a radio frequency transmitter, receiver, or transceiver 609 is included. In some embodiments, the transmitter, receiver, or transceiver 609 operates in the ISM (Industry, Science, and Medicine) radio frequency spectrum. In some embodiments, an internal antenna 610 is also included. In some embodiments, the antenna 610 is a strip antenna on the circuit board 604. The radio frequency component may implement low-power communication protocols such as Bluetooth 4.0 or ANT+. In some embodiments, transmitter, receiver, or transceiver 609 is an infrared transmitter, receiver, or transceiver.

In some embodiments, transmitter, receiver, or transceiver 609 is in electrical communication with circuit 606. In such embodiments, it may receive commands from an external transmitter and instruct the circuit 606 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 606 to turn on or off the LEDs. In some embodiments, transmitter, receiver, or transceiver 609 transmits signals to an external receiver indicating, for example, the charge level of the power source 607, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 611 is in electrical communication with circuit 606. LED 611 indicates the charge level of the power source 607, for example by flashing, changing color, or varying in intensity. In some embodiments, LED 611 may indicate that a target optical dose level has been transmitted into the intraoral cavity. In some embodiments, a buzzer or other audio output device 612 indicates charge or dose level by beeping or buzzing.

Figure 7:
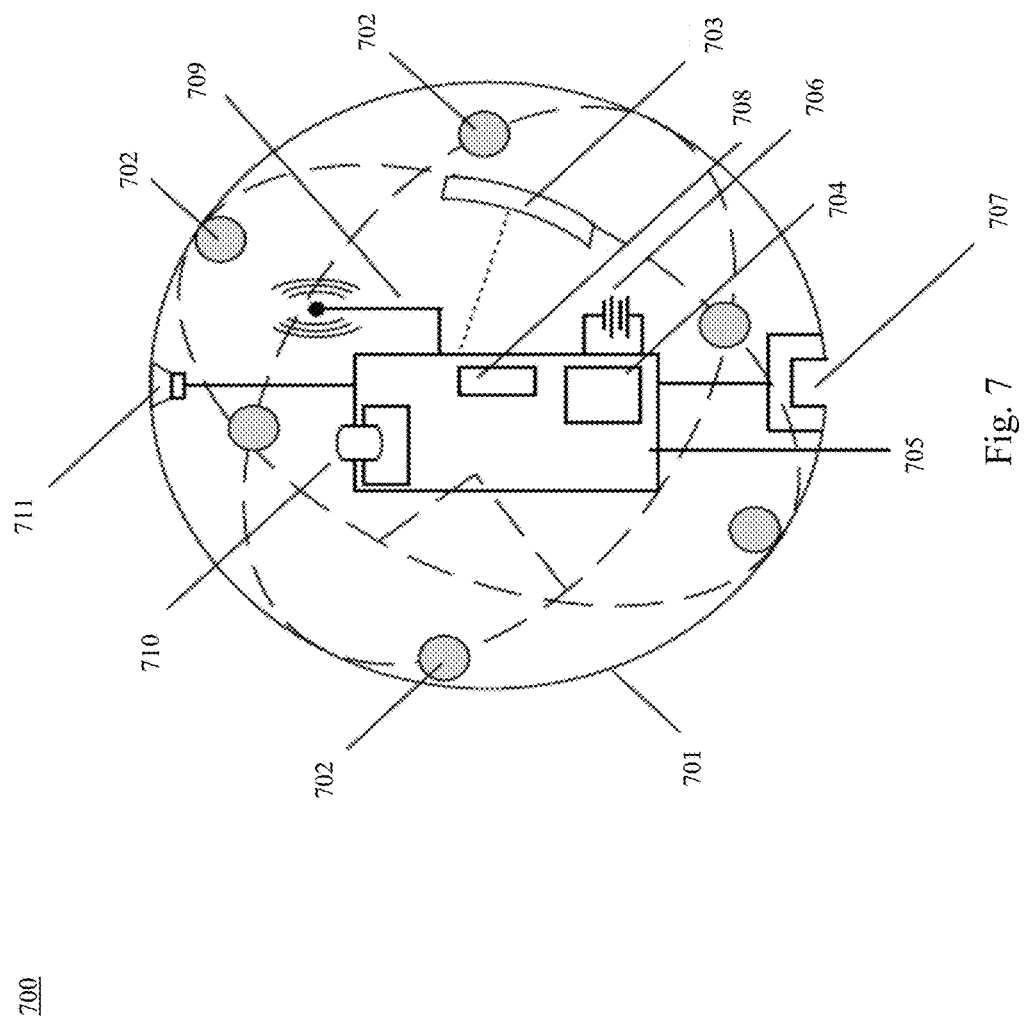
FIG. 7 is an interior schematic view of a device for intraoral application of light according to embodiments of the present disclosure.

Referring to FIG. 7, an interior view of a substantially spherical embodiment is provided. It will be appreciated that the exemplary components described with reference to FIGS. 6-7 may be combined in various combinations to form additional embodiments. A generally spherical optical diffuser 701 is illuminated at one end by one or more light sources 702 arrayed around the diffuser. The optical diffuser forms a shell around the other components, and at least a portion of its outer surface is transparent. In various embodiments, light sources 702 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. LEDs 702 may be placed on the diffuser, embedded within the diffuser, or arrayed within the interior of diffuser 701. The optical diffuser distributes light substantially radially. In some embodiments, the light diffuser may be oblate or prolate spheroidal in shape in order to encourage interaction by an animal and assist in the distribution of light into the oral cavity. In some embodiments, diffuser 701 may be substantially or completely transparent.

In some embodiments, the LEDs radiate light at a wavelength of about 400 nm to about 1,000 nm. In some embodiments, one or more LEDs primarily radiate light at about 455 nm, e.g. blue light, while other LEDs radiate light at about 815 nm, e.g., near infrared light.

Diffuser 701 is coupled to one or more strain sensors 703, such as a strain gauge, piezo polymer strain sensor, NITINOL wire, or variable resistive wire that sense radial or circumferential extensive or compressive strain due to compression of the diffuser. These sensors may be overlaid on the diffuser or embedded within it. In some embodiments, the sensor may be deposited within the interior of the diffuser to sense its compressive or flexural strain. In some embodiments, the sensor may additionally comprise a piezoceramic sensor such as a PZT (lead zirconate) sensor, a piezo sensor such as those found in piezo buzzers, or a flextentional transducer. These sensors sense when the optical diffuser is squeezed by the closing of an animal's jaws around at least some portion of the diffuser. The sensor(s) is electrically coupled to a circuit 704 that turns on the LED when the output of the sensor exceeds a preset value indicative of a biting action that compresses or flexes the optical diffuser.

It will be appreciated that circuit 704 may have various designs, and may comprise, e.g., a voltage comparator. In some embodiments, circuit 704 comprises a microcontroller programmed to turn on the LED when the output of the sensor exceeds a predetermined value indicative of a biting action that compresses or flexes the optical diffuser. If the circuit 704 comprises a microcontroller said microcontroller may monitor the charging level of the power source 706. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 704 includes an analog timing circuit comprising a 555 one-shot timer, a CMOS 4060 binary counter, or other analog components and circuits adapted to provide timed activation of the LEDs. In some embodiments, circuit 704 includes a microcontroller having one or more internal counter or timers, software timing loops, or interfaces to outboard counter or timer circuits.

The electronics are contained substantially within the optical diffuser 701. The electronics are powered by batteries 706, which in some embodiments are Lithium ion AA batteries. The batteries may be manually replaceable, or may be charged inductively through an inductive coupling port 707 and associated circuitry.

In some embodiments, a radio frequency transmitter, receiver, or transceiver 708 is in electrical communication with circuit 704. In some embodiments, the transmitter, receiver, or transceiver 708 operates in the ISM (Industry, Science, and Medicine) radio frequency spectrum. In some embodiments, an internal antenna 709 is also included. In some embodiments, the antenna 709 is a strip antenna on the circuit board 705. The radio frequency component may implement low-power communication protocols such as Bluetooth 4.0 or ANT+. In some embodiments, transmitter, receiver, or transceiver 708 is an infrared transmitter, receiver, or transceiver.

In some embodiments, transmitter, receiver, or transceiver 708 is in electrical communication with circuit 704. In such embodiments, it may receive commands from an external transmitter and instruct the circuit 704 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 704 to turn on or off the LEDs. In some embodiments, transmitter, receiver, or transceiver 708, transmits signals to an external receiver indicating, for example, the charge level of the power source 706, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 710 is in electrical communication with circuit 704. LED 710 indicates the charge level of the power source 706, for example by flashing, changing color, or varying in intensity. In some embodiments, LED 710 may indicate that a target optical dose level has been transmitted into the intraoral cavity. In some embodiments, a buzzer or other audio output device 711 indicates charge or dose level by beeping or buzzing.

In some embodiments, a reservoir or pump may further be included to provide a taste attractant or medication to an animal. In some embodiments, the reservoir and pump are located within the outer shell while an opening is provided in the shell for a taste attractant or medication to be delivered to the exterior.

In various exemplary embodiments, multiple replaceable components are combined in a configuration suitable for use with a leash. For example, a tubular shaped handle may be provided that contains replaceable batteries, LEDs and a switch. A replaceable intraoral portion may attach in a rotatable coupling like a ball socket to the handle via a threaded collar. The ball joint allows the device to swivel when the dog has it in its mouth. The intraoral light device may be solid clear plastic and have a flat blade like shape. A bolt snap attached to the end of the handle allows the device to be clipped to a leash. A custom leash with multiple D loops allows the device to be clipped near the hand or at other points on the leash.

In some embodiments, a manual on/off switch is provided. In some embodiments, a slot for application of flavorings that are attractive to the animal is provided. A human may control light application from a plastic ball joint articulated light delivery system. Flavorings favorable to the animal or medications useful in therapy may be applied. Medications may include additives that enhance the effectiveness of light such as a peroxide to serve as a source of oxygen for singlet oxygen production. Medications may also include photodynamic coupling agents that expand the action of light to other bacteria using. Medications may also include fluoride, which provide therapy for reducing tooth decay. Medications may also include other agents that enhance the general health of the animal.

In some embodiments, a handle may be opened by removing a cap to allow access to and replacement of a battery. In some embodiments, the cap is threaded. Where handle and intraoral portions are coupled by a ball joint, the intraoral portion may rotate and tilt relative to the handle. A collar may fit over the intraoral portion to affix it to the handle. In some embodiments, a device may be clipped to a leash so as to allow a dog to bite the intraoral portion of the device.

Figure 8:
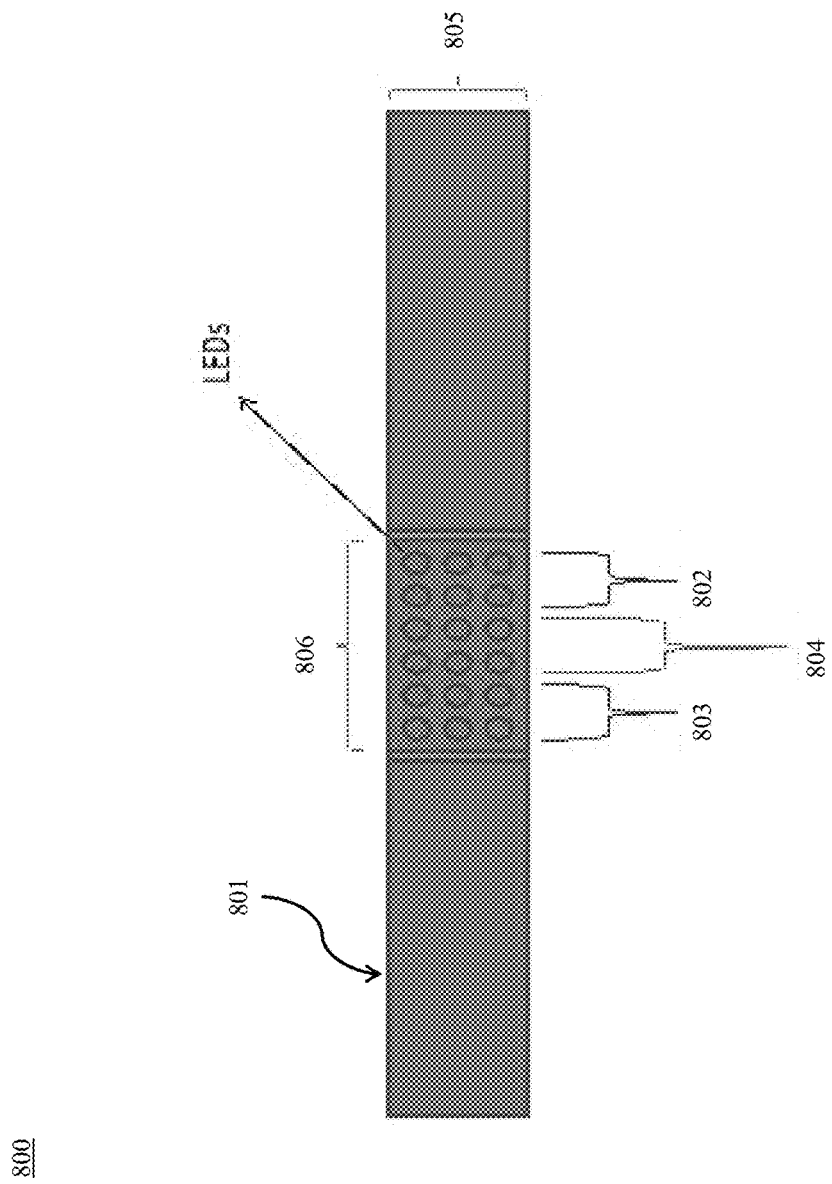
FIG. 8 depicts a device for intraoral application of light according to embodiments of the present disclosure.

Referring to FIG. 8, another exemplary device according to the present disclosure is illustrated. Strap 801 includes a plurality of embedded light sources. In various embodiments, light sources may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. Various embodiments include LEDs positioned to expose a dog's left teeth 802, LEDs positioned to expose a dog's right teeth 803, and LEDs positioned to expose a dog's tongue 804. In such embodiments, a dog may bite the strap, thereby placing the embedded LEDs 802 . . . 804 in the oral cavity. In some embodiments, the strap has a width 805 of about 2 inches. In some embodiments, the region containing LEDs has a length 806 of about 3.5 inches. However, it will be appreciated that various dimensions may be selected according to the size of the dog for which the strap is adapted. In some embodiments, strap 801 is integral to a leash.

In other exemplary devices according to the present a spherical handle is provided that contains replaceable batteries and a switch. A replaceable intraoral portion may be attached thereto and comprises a clear plastic cylinder. In some embodiments, LEDs are contained in the handle, while in some embodiments LEDs are contained in the intraoral portion. The intraoral portion and the handle may be joined by threads. In some embodiments, the handle is sized so as to be too large to fit in an animal's mouth while the animal is biting the intraoral portion. A strap may extend from the handle and may be held by a person, or coupled to a leash by a clip.

In various embodiments, a substantially spherical handle contains replaceable batteries, LEDs and an on/off button. In some embodiments, the spherical housing separates at the center to access the batteries. In some embodiment, the replaceable intraoral portion is a hollow, tubular shaped thermoplastic part. In some embodiments, the intraoral portion threads into the spherical housing. A strap loop may serve as a handle and allows the intraoral device to be held by a dog at any angle. In some embodiments, a bolt snap attached to the end of the strap allows the device to be clipped to a leash. A leash with multiple D loops may allow the device to be clipped near the hand or at other points on the leash.

Figure 9:
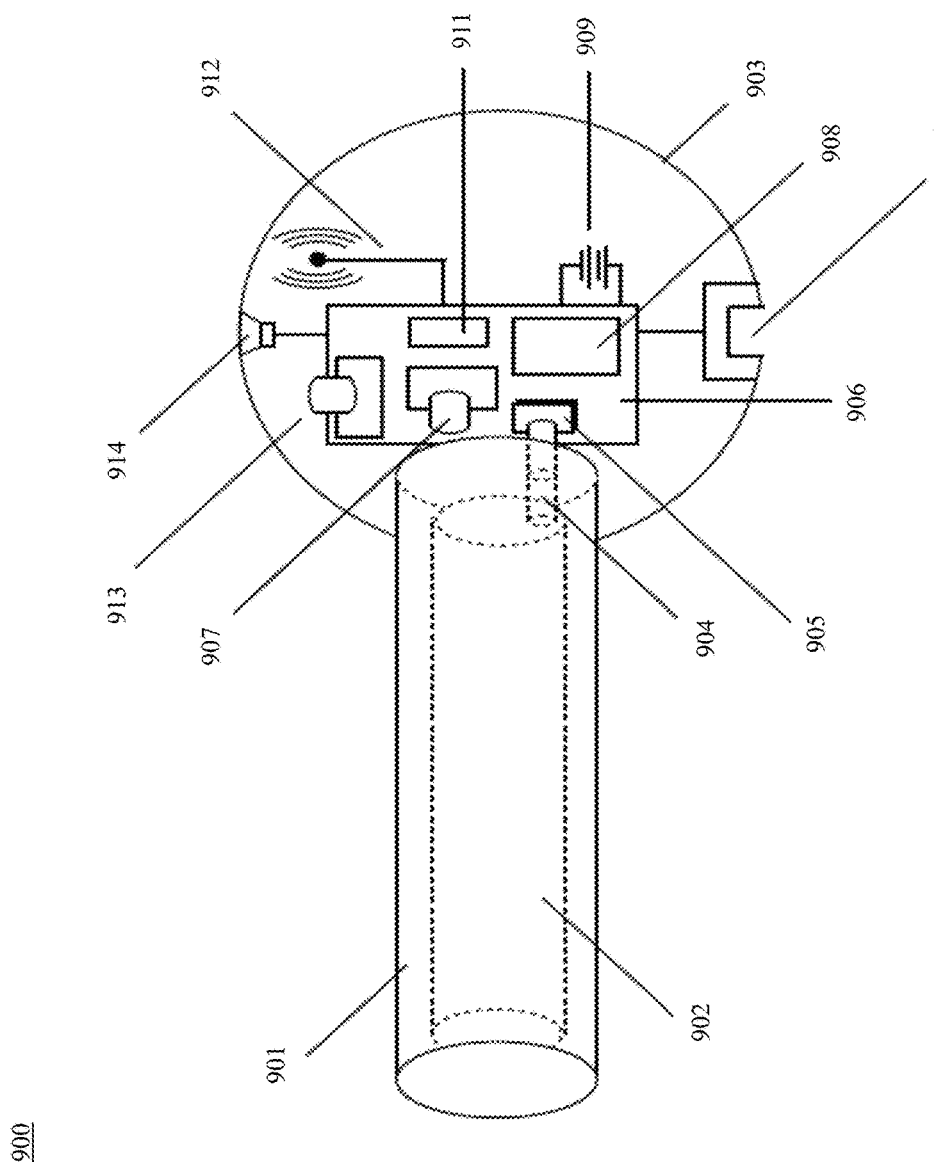
FIG. 9 is an interior schematic view of a device for intraoral application of light according to embodiments of the present disclosure.

Referring now to FIG. 9, an interior schematic view of a two part device according to the present disclosure is provided. An optical diffuser 901 having an inner cavity 902 is illuminated at one end by one or more light sources 907. The optical diffuser 901 and handle portion 903 form a shell around the other components, and at least a portion of the outer surface of the optical diffuser is transparent. In various embodiments, light sources 907 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. In some embodiments, an optical coupler may be placed between the LED(s) and optical diffuser 901 to improve the optical output by capturing more of the LED output and directing it into the diffuser. In some embodiments, the LED(s) may be set in a reflective or retroreflective optical reflector in order to direct more of the LED light into the optical diffuser. In some embodiments, the optical diffuser is flexible, and generally distributes light radially. In some embodiments, the optical diffuser additionally distributes light axially. In some embodiments, optical diffuser 901 comprises one or more light guides or waveguides.

In some embodiments, the light diffuser is ovoid in cross section. In some embodiments, the light diffuser has an annular cross section. In some embodiments, the light diffuser is toroidal in shape. In some embodiments, the light diffuser has a parallelepiped shape. It will be appreciated that various shapes are suitable for encouraging interaction by the animal and distributing light into the oral cavity.

In some embodiments, the LEDs radiate light at a wavelength of about 400 nm to about 1,000 nm. In some embodiments, one or more LEDs primarily radiate light at about 455 nm, e.g., blue light, while other LEDs radiate light at about 815 nm, e.g., near infrared light.

The cavity 902 is coupled via a port to a pressure sensor 905, such as a solid state pressure sensor. In some embodiments, the pressure sensor may be a pressure switch. The pressure sensor senses when the flexible optical diffuser is squeezed by the closing of an animal's jaws around at least some portion of the diffuser. The pressure sensor may be mounted on a circuit board 906, and its output provided to a circuit 908 that turns on the LEDs when the output of the pressure sensor exceeds a preset value indicative of a biting action that compresses or flexes the optical diffuser.

One of skill in the art will appreciate that circuit 908 may have various designs, and may comprise, e.g., a voltage comparator. Alternatively, circuit 908 comprises a microcontroller programmed to turn on the LEDs when the output of the pressure sensor exceeds a predetermined value indicative of a biting action that compresses or flexes the optical diffuser, or when the microcontroller senses that the output of the pressure switch goes high or low. If the circuit 908 comprises a microcontroller, the microcontroller may monitor the charging level of the power source 909. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 908 includes an analog timing circuit comprising a 555 one-shot timer, a CMOS 4060 binary counter, or other analog components and circuits adapted to provide timed activation of the LEDs. In some embodiments, circuit 908 includes a microcontroller having one or more internal counter or timers, software timing loops, or interfaces to outboard counter or timer circuits.

The electronics are contained substantially in housing 903 that is mechanically and optically coupled to optical diffuser 901. The electronics are powered by batteries 909, which in some embodiment are Lithium ion AA batteries. The batteries may be manually replaceable, or may be charged inductively through an inductive coupling port 910 and associated circuitry.

In some embodiments, a radio frequency transmitter, receiver, or transceiver 911 is included. In some embodiments, the transmitter, receiver, or transceiver 911 operates in the ISM (Industry, Science, and Medicine) radio frequency spectrum. In some embodiments, an internal antenna 912 is also included. In some embodiments, the antenna 912 is a strip antenna on the circuit board 906. The radio frequency component may implement low-power communication protocols such as Bluetooth 4.0 or ANT+. In some embodiments, transmitter, receiver, or transceiver 911 is an infrared transmitter, receiver, or transceiver.

In some embodiments, transmitter, receiver, or transceiver 911 is in electrical communication with circuit 908. In such embodiments, it may receive commands from an external transmitter and instruct the circuit 908 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 908 to turn on or off the LEDs. In some embodiments, transmitter, receiver, or transceiver 1911, transmits signals to an external receiver indicating, for example, the charge level of the power source 909, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 913 is in electrical communication with circuit 908. LED 913 indicates the charge level of the power source 909, for example by flashing, changing color, or varying in intensity. In some embodiments, LED 913 may indicate that a target optical dose level has been transmitted into the intraoral cavity. In some embodiments, a buzzer or other audio output device 914 indicates charge or dose level by beeping or buzzing.

Figure 10:
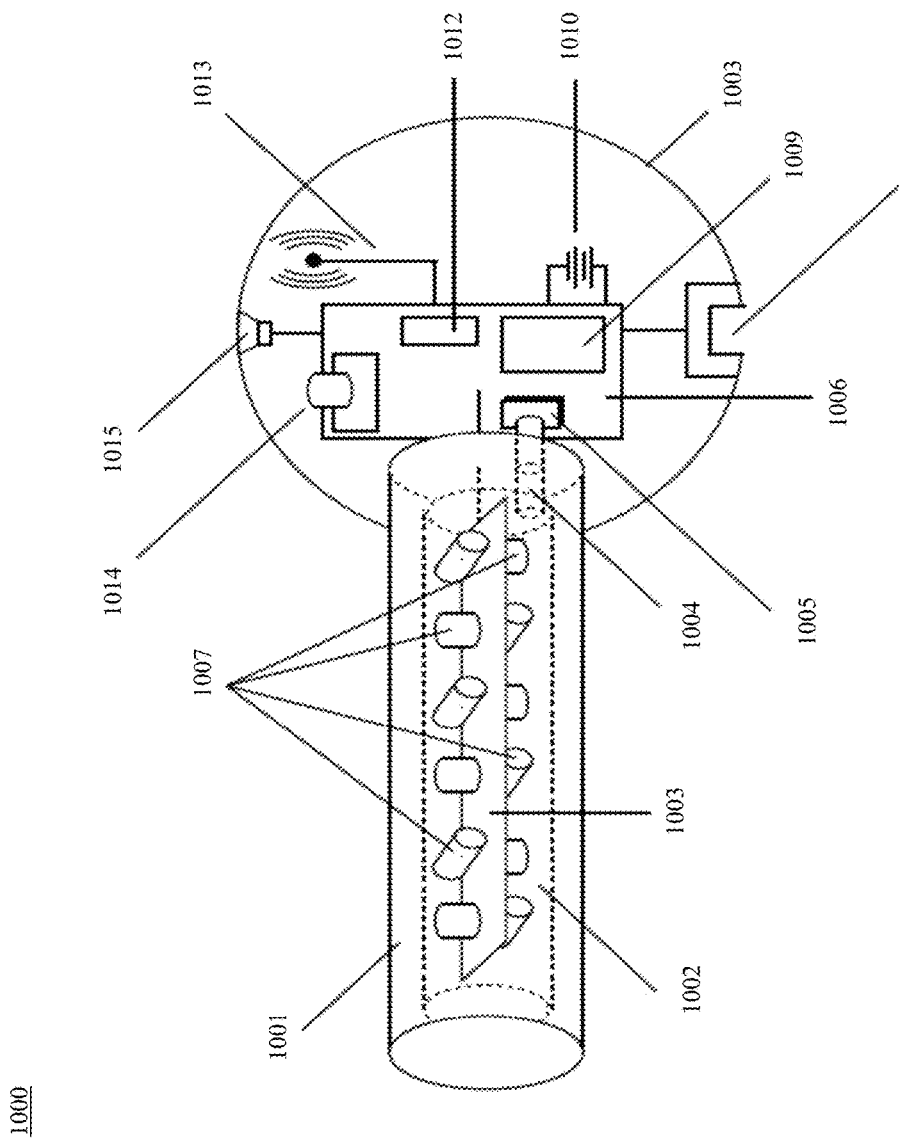
FIG. 10 is an interior schematic view of a device for intraoral application of light according to embodiments of the present disclosure.

Referring now to FIG. 10, an interior schematic view of a two part device according to the present disclosure is provided. An optical diffuser 1001 having an inner cavity 1002 is illuminated at one end by one or more light sources 1007. The optical diffuser 1001 and handle portion 1003 form a shell around the other components, and at least a portion of the outer surface of the optical diffuser is transparent. In various embodiments, light sources 1007 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. In some embodiments, the optical diffuser is flexible, and generally distributes light radially. In some embodiments, the optical diffuser additionally distributes light axially. In some embodiments, optical diffuser 1001 comprises one or more light guides or waveguides.

In some embodiments, the light diffuser is ovoid in cross section. In some embodiments, the light diffuser has an annular cross section. In some embodiments, the light diffuser is toroidal in shape. In some embodiments, the light diffuser has a parallelepiped shape. It will be appreciated that various shapes are suitable for encouraging interaction by the animal and distributing light into the oral cavity.

In some embodiments, the LEDs radiate light at a wavelength of about 400 nm to about 1,000 nm. In some embodiments, one or more LEDs primarily radiate light at about 455 nm, e.g., blue light, while other LEDs radiate light at about 815 nm, e.g., near infrared light.

The cavity 1002 is coupled via a port to a pressure sensor 1005, such as a solid state pressure sensor. In some embodiments, the pressure sensor may be a pressure switch. The pressure sensor senses when the flexible optical diffuser is squeezed by the closing of an animal's jaws around at least some portion of the diffuser. The pressure sensor may be mounted on a circuit board 1006, and its output provided to a circuit 1009 that turns on the LEDs when the output of the pressure sensor exceeds a preset value indicative of a biting action that compresses or flexes the optical diffuser. In some embodiments, pressure sensor 1005 may be mounted along with the LEDs on circuit board or mounting structure 1003.

One of skill in the art will appreciate that circuit 1009 may have various designs, and may comprise, e.g., a voltage comparator. Alternatively, circuit 1009 comprises a microcontroller programmed to turn on the LEDs when the output of the pressure sensor exceeds a predetermined value indicative of a biting action that compresses or flexes the optical diffuser, or when the microcontroller senses that the output of the pressure switch goes high or low. If the circuit 1009 comprises a microcontroller, the microcontroller may monitor the charging level of the power source 1010. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 1009 includes an analog timing circuit comprising a 555 one-shot timer, a CMOS 4060 binary counter, or other analog components and circuits adapted to provide timed activation of the LEDs. In some embodiments, circuit 1009 includes a microcontroller having one or more internal counter or timers, software timing loops, or interfaces to outboard counter or timer circuits.

The electronics are contained substantially in housing 1003 that is mechanically and optically coupled to optical diffuser 1001. The electronics are powered by batteries 1010, which in some embodiment are Lithium ion AA batteries. The batteries may be manually replaceable, or may be charged inductively through an inductive coupling port 1011 and associated circuitry.

In some embodiments, a radio frequency transmitter, receiver, or transceiver 1012 is included. In some embodiments, the transmitter, receiver, or transceiver 1012 operates in the ISM (Industry, Science, and Medicine) radio frequency spectrum. In some embodiments, an internal antenna 1013 is also included. In some embodiments, the antenna 1013 is a strip antenna on the circuit board 1006. The radio frequency component may implement low-power communication protocols such as Bluetooth 4.0 or ANT+. In some embodiments, transmitter, receiver, or transceiver 1012 is an infrared transmitter, receiver, or transceiver.

In some embodiments, transmitter, receiver, or transceiver 1012 is in electrical communication with circuit 1009. In such embodiments, it may receive commands from an external transmitter and instruct the circuit 1009 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 1009 to turn on or off the LEDs. In some embodiments, transmitter, receiver, or transceiver 1012, transmits signals to an external receiver indicating, for example, the charge level of the power source 1010, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 1014 is in electrical communication with circuit 1009. LED 1014 indicates the charge level of the power source 1010, for example by flashing, changing color, or varying in intensity. In some embodiments, LED 1014 may indicate that a target optical dose level has been transmitted into the intraoral cavity. In some embodiments, a buzzer or other audio output device 1015 indicates charge or dose level by beeping or buzzing.

Figure 11:
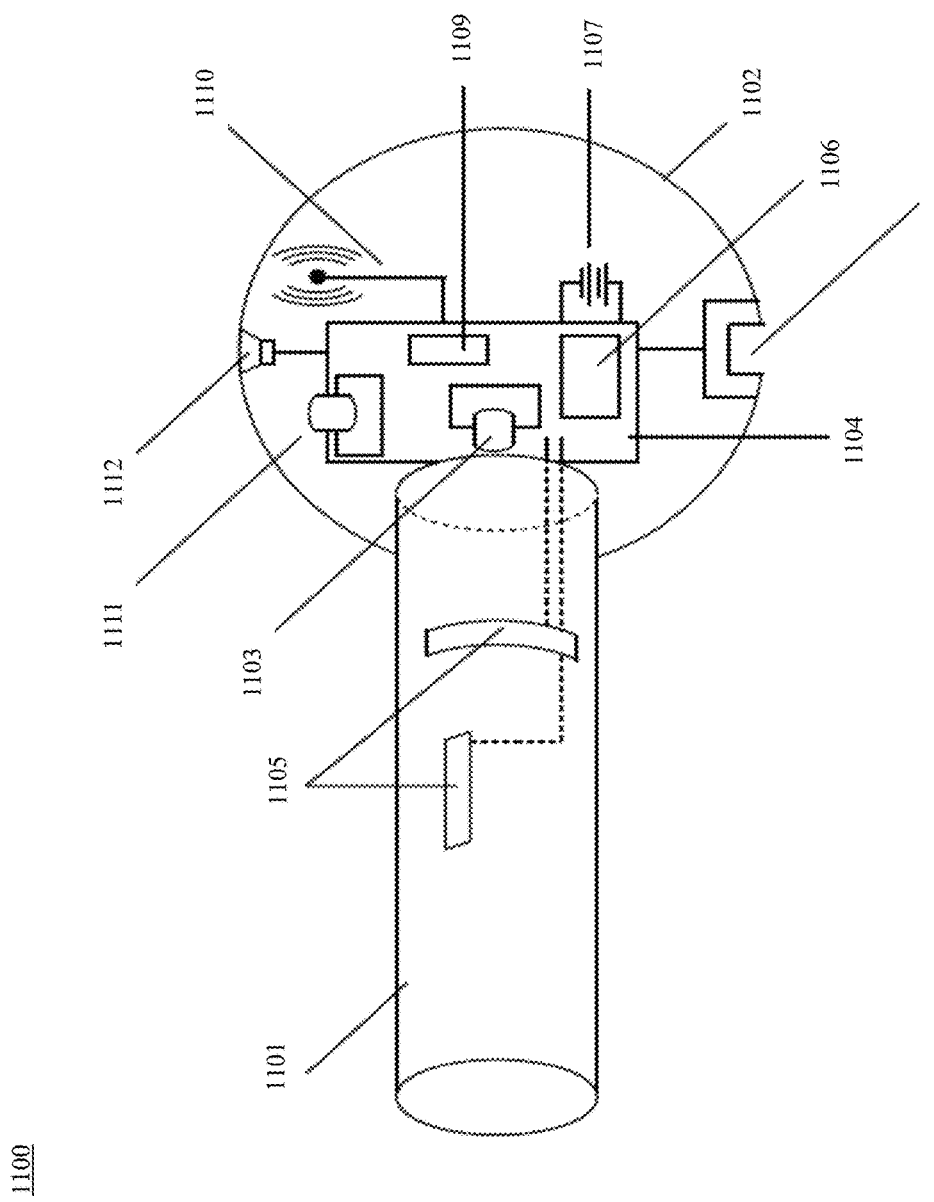
FIG. 11 is an interior schematic view of a device for intraoral application of light according to embodiments of the present disclosure.

Referring now to FIG. 11, an interior schematic view of a two part device according to the present disclosure is provided. An optical diffuser 1101 is illuminated at one end by one or more light sources 1103. The optical diffuser 1101 and handle portion 1102 form a shell around the other components, and at least a portion of the outer surface of the optical diffuser is transparent. In various embodiments, light sources 1103 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. In some embodiments, an optical coupler may be placed between the LED(s) and optical diffuser 1101 to improve the optical output by capturing more of the LED output and directing it into the diffuser. In some embodiments, the LED(s) may be set in a reflective or retroreflective optical reflector in order to direct more of the LED light into the optical diffuser. In some embodiments, the optical diffuser is flexible, and generally distributes light radially. In some embodiments, the optical diffuser additionally distributes light axially. In some embodiments, optical diffuser 1101 comprises one or more light guides or waveguides.

In some embodiments, the light diffuser is ovoid in cross section. In some embodiments, the light diffuser has an annular cross section. In some embodiments, the light diffuser is toroidal in shape. In some embodiments, the light diffuser has a parallelepiped shape. It will be appreciated that various shapes are suitable for encouraging interaction by the animal and distributing light into the oral cavity.

In some embodiments, the LEDs radiate light at a wavelength of about 400 nm to about 1,000 nm. In some embodiments, one or more LEDs primarily radiate light at about 455 nm, e.g., blue light, while other LEDs radiate light at about 815 nm, e.g., near infrared light.

The diffuser 1101 is coupled to one or more strain sensors 1105, such as a strain gauge, piezo polymer strain sensor, NITINOL wire, or variable resistive wire. Such strain sensors sense axial, radial, or circumferential extensive or compressive strain or shear due to compression or flexion of the diffuser. These sensors may be overlaid on the diffuser or embedded within it. In some embodiments, the sensor are deposited along or substantially parallel to the diffuser's major axis. In such embodiments, the sensors sense compressive or flexural strain. In some embodiments, the sensors additionally comprise a piezoceramic sensor such as a PZT (lead zirconate) sensor, or a piezo sensor such as those found in piezo buzzers. These sensors sense when the optical diffuser is squeezed by the closing of an animal's jaws around at least some portion of the diffuser. The sensor(s)' output is electrically coupled to a circuit 1106 that turns on the LED when the output of the sensor exceeds a preset value indicative of a biting action that compresses or flexes the optical diffuser.

One of skill in the art will appreciate that circuit 1106 may have various designs, and may comprise, e.g., a voltage comparator. Alternatively, circuit 1106 comprises a microcontroller programmed to turn on the LEDs when the output of the pressure sensor exceeds a predetermined value indicative of a biting action that compresses or flexes the optical diffuser, or when the microcontroller senses that the output of the pressure switch goes high or low. If the circuit 1106 comprises a microcontroller, the microcontroller may monitor the charging level of the power source 1107. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 1106 includes an analog timing circuit comprising a 555 one-shot timer, a CMOS 4060 binary counter, or other analog components and circuits adapted to provide timed activation of the LEDs. In some embodiments, circuit 1106 includes a microcontroller having one or more internal counter or timers, software timing loops, or interfaces to outboard counter or timer circuits.

The electronics are contained substantially in housing 1102 that is mechanically and optically coupled to optical diffuser 1101. The electronics are powered by batteries 1107, which in some embodiment are Lithium ion AA batteries.

The batteries may be manually replaceable, or may be charged inductively through an inductive coupling port 1108 and associated circuitry.

In some embodiments, a radio frequency transmitter, receiver, or transceiver 1109 is included. In some embodiments, the transmitter, receiver, or transceiver 1109 operates in the ISM (Industry, Science, and Medicine) radio frequency spectrum. In some embodiments, an internal antenna 1110 is also included. In some embodiments, the antenna 1110 is a strip antenna on the circuit board 1104. The radio frequency component may implement low-power communication protocols such as Bluetooth 4.0 or ANT+. In some embodiments, transmitter, receiver, or transceiver 1109 is an infrared transmitter, receiver, or transceiver.

In some embodiments, transmitter, receiver, or transceiver 1109 is in electrical communication with circuit 1106. In such embodiments, it may receive commands from an external transmitter and instruct the circuit 1106 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 1106 to turn on or off the LEDs. In some embodiments, transmitter, receiver, or transceiver 1109, transmits signals to an external receiver indicating, for example, the charge level of the power source 1107, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 1111 is in electrical communication with circuit 1106. LED 1111 indicates the charge level of the power source 1107, for example by flashing, changing color, or varying in intensity. In some embodiments, LED 1111 may indicate that a target optical dose level has been transmitted into the intraoral cavity. In some embodiments, a buzzer or other audio output device 1112 indicates charge or dose level by beeping or buzzing.

Figure 12:
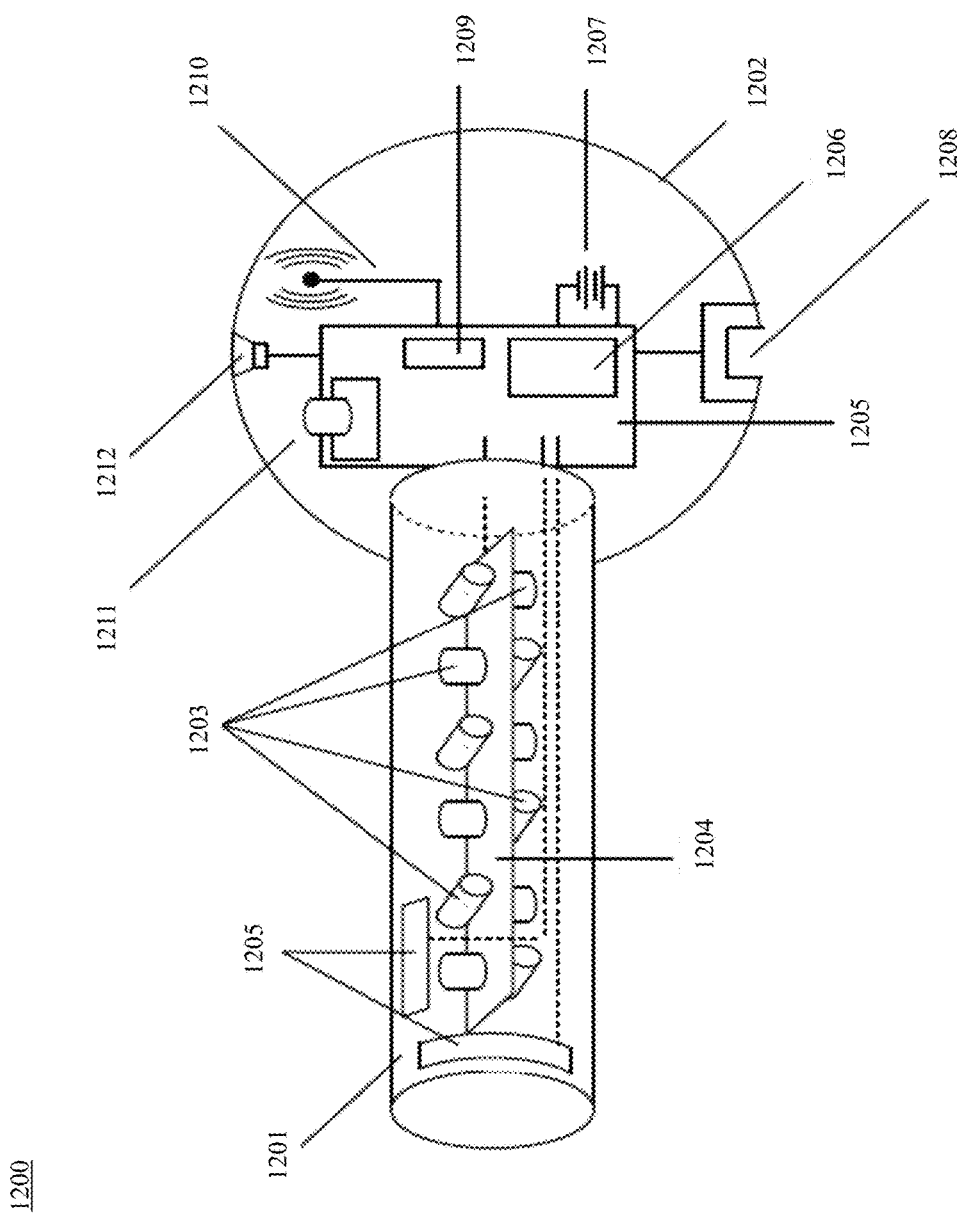
FIG. 12 is an interior schematic view of a device for intraoral application of light according to embodiments of the present disclosure.

Referring now to FIG. 12, an interior schematic view of a two part device according to the present disclosure is provided. An optical diffuser 1201 is illuminated at one end by one or more light sources 1207. The optical diffuser 1201 and handle portion 1202 form a shell around the other components, and at least a portion of the outer surface of the optical diffuser is transparent. In various embodiments, light sources 1207 may comprise, e.g., one or more light-emitting diodes (LEDs), organic light emitting diodes (OLEDs), or electroluminescent (EL) lights. For simplicity of explanation, and not limitation, various embodiments are described in terms of LEDs although it will be appreciated that alternatives such as the above may be substituted in those embodiments. In some embodiments, the optical diffuser is flexible, and generally distributes light radially. In some embodiments, the optical diffuser additionally distributes light axially. In some embodiments, optical diffuser 1201 comprises one or more light guides or waveguides.

In some embodiments, the light diffuser is ovoid in cross section. In some embodiments, the light diffuser has an annular cross section. In some embodiments, the light diffuser is toroidal in shape. In some embodiments, the light diffuser has a parallelepiped shape. It will be appreciated that various shapes are suitable for encouraging interaction by the animal and distributing light into the oral cavity.

In some embodiments, the LEDs radiate light at a wavelength of about 400 nm to about 1,000 nm. In some embodiments, one or more LEDs primarily radiate light at about 455 nm, e.g., blue light, while other LEDs radiate light at about 815 nm, e.g., near infrared light.

The diffuser 1201 is coupled to one or more strain sensors 1205, such as a strain gauge, piezo polymer strain sensor, NITINOL wire, or variable resistive wire that sense axial, radial, or circumferential extensive or compressive strain or shear due to compression or flexion of the diffuser. These sensors may be overlaid on the diffuser or embedded within it. In some embodiments, the sensor may be deposited along or substantially parallel to the diffuser's major axis and sense its compressive or flexural strain. In some embodiments, the sensors additionally comprise a piezoceramic sensor such as a PZT (lead zirconate) sensor, or a piezo sensor such as those found in piezo buzzers. These sensors sense when the optical diffuser is squeezed by the closing of an animal's jaws around at least some portion of the diffuser. The sensor(s)' output is electrically coupled to a circuit 1206 that turns on the LED when the output of the sensor exceeds a preset value indicative of a biting action that compresses or flexes the optical diffuser.

One of skill in the art will appreciate that circuit 1206 may have various designs, and may comprise, e.g., a voltage comparator. Alternatively, circuit 1206 comprises a microcontroller programmed to turn on the LEDs when the output of the pressure sensor exceeds a predetermined value indicative of a biting action that compresses or flexes the optical diffuser, or when the microcontroller senses that the output of the pressure switch goes high or low. If the circuit 1206 comprises a microcontroller, the microcontroller may monitor the charging level of the power source 1207. In some embodiments, an electrical switch is mounted to the housing or the diffuser that itself may turn on or off the LED(s).

In some embodiments, timed dosage such as that described with reference to FIGS. 3-4 is provided. In some such embodiments, circuit 1206 includes an analog timing circuit comprising a 555 one-shot timer, a CMOS 4060 binary counter, or other analog components and circuits adapted to provide timed activation of the LEDs. In some embodiments, circuit 1206 includes a microcontroller having one or more internal counter or timers, software timing loops, or interfaces to outboard counter or timer circuits.

The electronics are contained substantially in housing 1202 that is mechanically and optically coupled to optical diffuser 1201. The electronics are powered by batteries 1207, which in some embodiment are Lithium ion AA batteries. The batteries may be manually replaceable, or may be charged inductively through an inductive coupling port 1208 and associated circuitry.

In some embodiments, a radio frequency transmitter, receiver, or transceiver 1209 is included. In some embodiments, the transmitter, receiver, or transceiver 1209 operates in the ISM (Industry, Science, and Medicine) radio frequency spectrum. In some embodiments, an internal antenna 1210 is also included. In some embodiments, the antenna 1210 is a strip antenna on the circuit board 1205. The radio frequency component may implement low-power communication protocols such as Bluetooth 4.0 or ANT+. In some embodiments, transmitter, receiver, or transceiver 1209 is an infrared transmitter, receiver, or transceiver.

In some embodiments, transmitter, receiver, or transceiver 1209 is in electrical communication with circuit 1206. In such embodiments, it may receive commands from an external transmitter and instruct the circuit 1206 to turn on or off the LED(s). Such commands may originate from an external control device, such as a dedicated remote control or a mobile computing device such as a smart phone. In some embodiments, a smart phone app is provided that receives user input and sends commands wirelessly, instructing circuit 1206 to turn on or off the LEDs. In some embodiments, transmitter, receiver, or transceiver 1209, transmits signals to an external receiver indicating, for example, the charge level of the power source 1207, whether the LEDs are turned on, or the optical dose transmitted into the intraoral cavity. In some embodiments, such signals are received by an external control device, such as a dedicated remote control or a mobile computing device such as a smart phone. In some embodiments, a smart phone app is provided that provides output to a user based on the received signals.

In some embodiments, an LED 1211 is in electrical communication with circuit 1206. LED 1211 indicates the charge level of the power source 1207, for example by flashing, changing color, or varying in intensity. In some embodiments, LED 1211 may indicate that a target optical dose level has been transmitted into the intraoral cavity. In some embodiments, a buzzer or other audio output device 1212 indicates charge or dose level by beeping or buzzing.

It will be appreciated that a variety of form factors are suitable for use according to the present disclosure. As described above, various embodiments have a substantially spherical form. In some embodiments, a leash extension is provided as the light delivery system. In some embodiments, hand-held toys are provided. For further example, devices according to the present disclosure may include a translucent doughnut shape having embedded LEDs, dog bone shape with embedded LEDs, or a half circle with embedded LEDs and an attached tether.

In further embodiments, a mouse-like toy is provided that lights when the animal bites it, suitable for use with cats. In yet further embodiments, a string- or rope-like light diffuser is provided that emits light at the specified wavelength and power. Some embodiments having a rope- or string-like form factor may comprise an electroluminescent (EL) wire as a light source. In some embodiments, an attractant such as catnip extract or a flavoring such as a bacon or tuna flavoring may be included to enhance animal interaction with the device.

The embodiments described above may also include reservoirs or pumps to provide a taste attractant with or without additional medications. These medications may include additives that enhance the effectiveness of light such as a peroxide as a source of oxygen for singlet oxygen production. Medications may also include photodynamic coupling agents that expand the action of light to other bacteria. Medications may also include agents such as fluoride that provide therapy for reducing tooth decay. Medications may also include other agents that enhance the general health of the animal.

It will be appreciated that a variety of materials are suitable for phototherapeutic devices according to the present disclosure. As describe above, various embodiments have a transparent or translucent shall in which various LEDs are positioned. In general, materials that are resilient to biting, nontoxic, durable, water-resistant, and substantially transparent to light of the wavelengths described herein are suitable. In some embodiments, the LEDs may be separately encapsulated in plastic so as to be water proof.

One exemplary material for an outer casing of a device according to the present disclosure is Tritan MX711. Tritan MX711 is a clear medical grade copolyester that is chemical and heat resistant.

Another exemplary material for an outer casing of a device according to the present disclosure is Trogamid MX 73. Trogamid MX 73 is an amorphous and microcrystalline transparent polyamide that is highly resistant to chemicals and stress-cracking. Trogamid MX 73 has a tensile modulus of about 1,400 MPa, a flexural modulus of about 1,700 MPa, and a Shore hardness (D) of about 81.

Another exemplary material for an outer casing of a device according to the present disclosure is SILBIONE LSR 4330. SILBIONE LSR 4330 is a healthcare grade liquid silicone rubber with high clarity and strength. Once cured, SILBIONE LSR 4330 has a Shore hardness (A) of about 30 to about 31, a tensile strength of about 1,400 to about 1,350 psi, an elongation of about 790% to about 750%, a tear strength of about 195 to about 205 Ppi, a 100% Modulus of about 190 to about 200 psi, a compression set of about 35% to about 10%, and a resiliency of about 62% to about 60%.

Animal phototherapeutic devices according to the present disclosure may be controlled in various ways. For example, a remote manual control may be provided via radiofrequency or infrared signals. Such manual remote controls may activate or deactivate the light source within a target. Such manual controls may be provided in addition to or in place of bite activated control. In some embodiments, animal phototherapeutic devices may be programmed with respect to dosage timing, intensity, or duration by remote control. In some embodiments, a smartphone app is provided that allows remote programming using a graphical user interface of a smart phone.

In various embodiments, an animal phototherapeutic device as described above may be combined with topically applied photosensitizer to extend the bacterial spectrum of species affected. For example, a methylene blue or toluidine blue mouth rinse may be used to reduce numbers of bacteria that do not contain porphyrins. Similarly, following a suitable oral dose of 5-aminolevulinic acid, irradiation by devices according to the present disclosure can be used to kill rapidly growing tissue such as cancerous or pre-cancerous lesions.

A mean survival fraction in canine dental plaque is expected to be similar to that of human dental plaque following exposure to blue light. For reference, blue light at 455 nm has been shown to kill about 28.5% of bacteria in human dental plaque. For further illustration, in one study, the genera most frequently isolated from canine plaque were *Porphyromonas* (20%), *Actinomyces* (12%), and *Neisseria* (10%).

Figure 13:
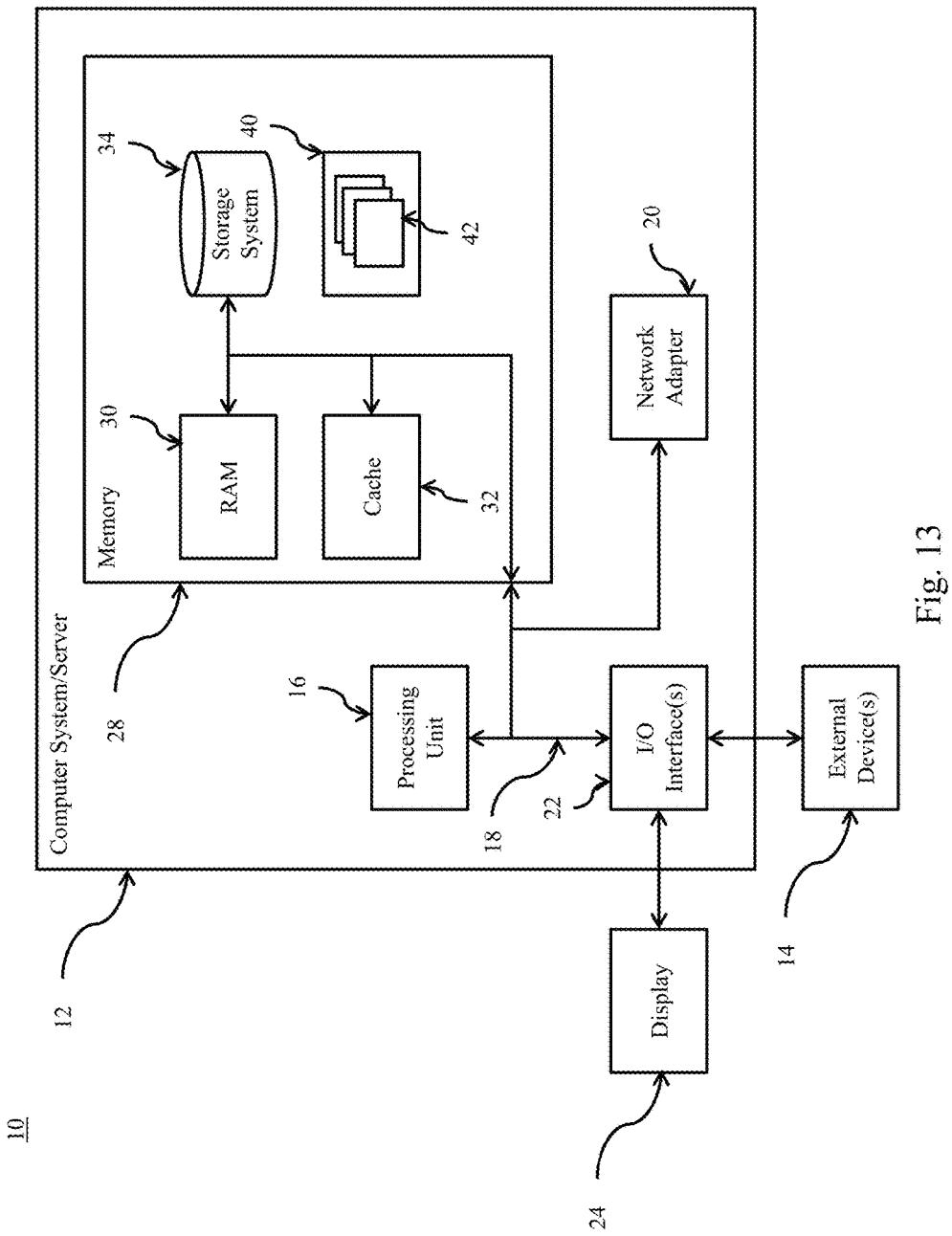
FIG. 13 depicts a computing node according to an embodiment of the present invention.

Referring now to FIG. 13, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 13, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device such as a mouse or touchpad, a display 24 such as a touchscreen, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a device, system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications, combinations, and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device comprising:
    a water-resistant shell adapted to resist intrusion of water when deployed in an oral cavity of an animal, the shell having an outer surface, the outer surface having one translucent region;
    at least one light-emitting diode disposed within the shell, the at least one light-emitting diode being adapted to emit light having a wavelength between 400 nm and 1,000 nm when powered, the at least one light-emitting diode being configured to provide an average light intensity of between 10 and 50 mW/cm$^2$ across the one translucent region of the outer surface circumferentially about the shell;
    a power source disposed within the shell;
    a switch disposed at least partially within the shell and adapted to control current flow from the power source to the at least one light-emitting diode; and
    a sensor operatively coupled to the switch and adapted to enable the switch upon detection of an animal bite.

2. The device of claim 1, wherein the at least one light-emitting diode is adapted to emit light having a wavelength between 400 nm and 700 nm when powered.

3. The device of claim 1, wherein the at least one light-emitting diode is adapted to emit light having a wavelength between 400 nm and 500 nm when powered.

4. The device of claim 1, wherein the at least one light-emitting diode is adapted to emit light having a wavelength of 455 nm when powered.

5. The device of claim 1, wherein the shell is substantially spherical.

6. The device of claim 1, wherein the shell comprises a handle portion and a diffuser portion, the one translucent region being located on the diffuser portion and the power source being disposed within handle portion.

7. The device of claim 6, wherein the handle portion is substantially cylindrical.

8. The device of claim 6, wherein the diffuser portion is substantially cylindrical, substantially conical, or substantially a truncated cone.

9. The device of claim 6, wherein the diffuser portion has a substantially circular cross section.

10. The device of claim 1, further comprising an inductive coupling port electrically coupled to the power source.

11. The device of claim 1, the sensor comprising a pressure sensor.

12. The device of claim 11, wherein the pressure sensor is adapted to activate the switch upon detection of pressure exceeding a predetermined value indicative of a biting action.

13. The device of claim 1, further comprising a strain sensor, the strain sensor being operatively coupled to the switch.

14. The device of claim 11, wherein the strain sensor is adapted to activate the switch upon detection of strain exceeding a predetermined value.

15. The device of claim 1, further comprising a strap, the shell being embedded in the strap.

16. The device of claim 1, further comprising an IR receiver, the IR receiver being operatively coupled to the switch.

17. The device of claim 16, the IR receiver being adapted to activate the switch upon detection of an IR control signal.

18. The device of claim 16, the IR receiver being adapted to deactivate the switch upon detection of an IR control signal.

19. The device of claim 1, further comprising an RF receiver, the RF receiver being operatively coupled to the switch.

20. The device of claim 19, the RF receiver being adapted to activate the switch upon receipt of a control signal.

21. The device of claim 19, the RF receiver being adapted to deactivate the switch upon receipt of a control signal.

22. The device of claim 1, further comprising an RF receiver, the RF receiver being operatively coupled to the switch, wherein the RF receiver comprises a Bluetooth receiver.

23. The device of claim 6, wherein the at least one light-emitting diode is disposed within the diffuser portion, and wherein the at least one light-emitting diode comprises more than one light emitting diode.

24. The device of claim 6, wherein the at least one light-emitting diode is disposed within the handle portion.

25. The device of claim 1, further comprising a reservoir containing a taste attractant adapted to encourage animal interaction with the device.

26. The device of claim 25, wherein the reservoir is in fluid communication with a pump adapted to dispose the contents of the reservoir on the outer surface.

27. The device of claim 1, the at least one light-emitting diode being configured to provide an average light intensity of 25 mW/cm$^2$ across the one translucent region of the outer surface.

28. A method comprising:
providing a device to a non-human animal, the device comprising
a water-resistant shell adapted to resist intrusion of water when deployed in an oral cavity of an animal, the shell having an outer surface, the outer surface having at least one translucent region,
at least one light-emitting diode disposed within the shell,
a power source disposed within the shell,
a switch disposed at least partially within the shell and adapted to control current flow from the power source to the at least one light-emitting diode, and
a sensor operatively coupled to the switch and adapted to enable the switch upon detection of an animal bite;
powering the at least one light-emitting diode from the power source, the at least one light-emitting diode thereby emitting light having a wavelength between 400 nm and 1,000 nm with an average light intensity of between 10 and 50 mW/cm$^2$ across the at least one translucent region of the outer surface of the device circumferentially about the shell.

29. The device of claim 1, further comprising:
a timer operatively coupled to the switch and adapted to disable the switch after a dose time has elapsed.

* * * * *